US006245517B1

(12) United States Patent
Chen et al.

(10) Patent No.: US 6,245,517 B1
(45) Date of Patent: Jun. 12, 2001

(54) RATIO-BASED DECISIONS AND THE QUANTITATIVE ANALYSIS OF CDNA MICRO-ARRAY IMAGES

(75) Inventors: Yidong Chen, Rockville, MD (US); Edward R. Dougherty, College Station, TX (US); Michael L. Bittner, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/407,021

(22) Filed: Sep. 28, 1999

Related U.S. Application Data

(60) Provisional application No. 60/102,365, filed on Sep. 29, 1998.

(51) Int. Cl.[7] .............................. C12Q 1/68; G01N 33/48; G01N 31/00; G06F 15/00
(52) U.S. Cl. .................................. 435/6; 702/20; 702/32; 712/200
(58) Field of Search ................................. 435/6; 702/20, 702/32; 712/200; 364/400

(56) References Cited

U.S. PATENT DOCUMENTS 4,282,405  8/1981  Taguchi .

OTHER PUBLICATIONS

Ridout, "A Comparison of Confidence Interval Methods for Dilution Series Experiments," *Biometrics* 50:289–296, 1994.

Zeltkevic, "Variance, Standard Deviation and Coefficient of Variation," http://web.mit.edu/10.001/Web/Course_Notes/Statistics_Notes/Visualization/node4.html, Apr. 1998.

Smith, "Applicative Programming," http://www.cc.gatech.edu/gvu/people/Phd/Ian/2360/lect5.html, Jan. 1995.

Edward R. Dougheryy, Yidong Chen, Sinan Batman, Michael L. Bittner, "Digital Measurement of Gene Expression in a cDNA Micro–array," SPIE, vol. 3034, Feb. 1997, pp. 68–72.

"Molecular Dynamics," *Molecular Dynamics, Inc.*, Sep. 1, 1998.

"What is an Array?", *Molecular Dynamics, Inc.*, Sep. 18, 1998.

DeRisi et al., "Use of a cDNA Microarray to Analyse Gene Expression Patterns in Human Cancer," *Nature Genetics*, vol. 14, Dec. 14, 1996, pp. 457–460.

Schena et al., "Parallel Human Genome Analysis: Microarray–Based Expression Monitoring of 1000 Genes," *Proc. Natl. Acad. Sci., USA*, vol. 93, Oct., 1996, pp. 10614–10619.

Schena et al., "Quantitative Monitoring of Gene Expression Patterns With a Complementary DNA Microarray," *Science*, vol. 270, Oct. 20, 1995.

*Primary Examiner*—John S. Brusca
*Assistant Examiner*—Young Kim
(74) *Attorney, Agent, or Firm*—Klarquist Sparkman Campbell Leigh & Whinston LLP

(57) ABSTRACT

Gene expression can be quantitatively analyzed by hybridizing fluor-tagged mRNA to targets on a cDNA micro-array. Comparison of gene expression levels arising from co-hybridized samples is achieved by taking ratios of average expression levels for individual genes. In an image-processing phase, a method of image segmentation identifies cDNA target sites in a cDNA micro-array image. The resulting cDNA target sites are analyzed based on a hypothesis test and confidence interval to quantify the significance of observed differences in expression ratios. In particular, the probability density of the ratio and the maximum-likelihood estimator for the distribution are derived, and an iterative procedure for signal calibration is developed.

20 Claims, 6 Drawing Sheets

(1 of 6 Drawing Sheet(s) Filed in Color)

TARGET SITE
TARGET MASK
TARGET PATCH

Detection result at α=0.0001

Detection result at α=0.05

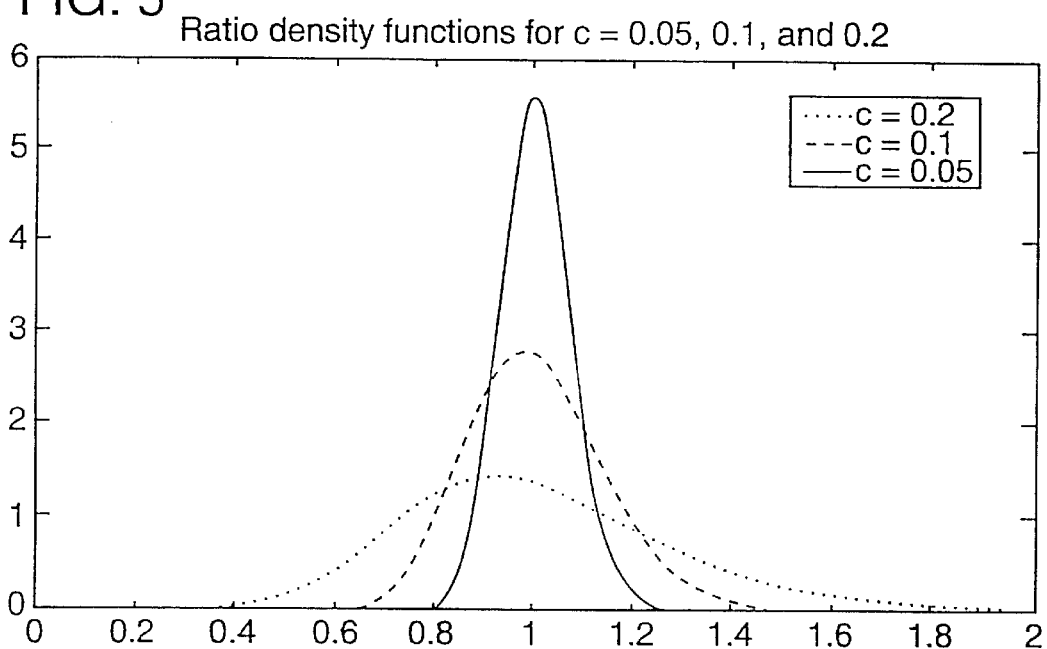
FIG. 5 Ratio density functions for c = 0.05, 0.1, and 0.2

RATIO-BASED DECISIONS AND THE QUANTITATIVE ANALYSIS OF CDNA MICRO-ARRAY IMAGES

RELATED APPLICATION DATA

This patent application claims the benefit of U.S. Provisional Application No. 60/102,365, filed Sep. 29, 1998, which is hereby incorporated by reference.

FIELD OF THE INVENTION

The invention relates to quantitative analysis of gene expression in cDNA micro-array images.

BACKGROUND OF THE INVENTION

The recent development of complementary DNA micro-array technology provides a powerful analytical tool for human genetic research (M. Schena, D. Shalon, R. W. Davis, and P. O. Brown, "Quantitative monitoring of gene expression patterns with a complementary DNA microarray," Science, 270(5235), 467–70, 1995). One of its basic applications is to quantitatively analyze fluorescence signals that represent the relative abundance of mRNA from two distinct tissue samples. cDNA micro-arrays are prepared by automatically printing thousands of cDNAs in an array format on glass microscope slides, which provide gene-specific hybridization targets. Two different samples (of mRNA) can be labeled with different fluors and then co-hybridized on to each arrayed gene. Ratios of gene-expression levels between the samples are calculated and used to detect meaningfully different expression levels between the samples for a given gene.

Biological Background and cDNA Micro-Array Technology

A cell relies on its protein components for a wide variety of its functions. The production of energy, the biosynthesis of all component macromolecules, the maintenance of cellular architecture and the ability to act upon intra and extracellular stimuli are all protein dependent. Each cell within an organism contains the information necessary to produce the entire repertoire of proteins which that organism can specify. This information is stored as genes within the organism's DNA genome. The number of human genes is estimated to be 30,000 to 100,000. Within any individual cell, only a portion of the possible gene set is present as protein. Some of the proteins present in a cell are likely to be present in all cells. These proteins serve functions required in every type of cell, and can be thought of as "housekeeping" proteins. Other proteins serve specialized functions only required in particular cell types. For example, muscle cells contain specialized proteins that form the dense contractile fibers of a muscle. Given that a large part of a cell's specific functionality is determined by the genes it is expressing, it is logical that transcription, the first step in the process of converting the genetic information stored in an organism's genome into protein, would be highly regulated by the control network that coordinates and directs cellular activity.

Regulation is readily observed in studies that scrutinize activities evident in cells configuring themselves for a particular function (specialization into a muscle cell) or state (active multiplication or quiescence). As cells alter their status, coordinate transcription of the protein sets required for this state can be observed. As a window both on cell status and on the system controlling the cell, detailed, global knowledge of the transcriptional state could provide a broad spectrum of information useful to biologists. Knowledge of when and in what types of cell the protein product of a gene of unknown function is expressed would provide useful clues as to the likely function of that gene. Determination of gene-expression patterns in normal cells could provide detailed knowledge of the way in which the control system achieves the highly coordinated activation and deactivation required for development and differentiation of a mature organism from a single fertilized egg. Comparison of gene expression patterns in normal and pathological cells could provide useful diagnostic "fingerprints" and help identify aberrant functions which would be reasonable targets for therapeutic intervention.

The ability to carry out studies in which the transcriptional state of a large number of genes is determined has, until recently, been severely inhibited by limitations on our ability to survey cells for the presence and abundance of a large number of gene transcripts in a single experiment. A primary limitation has been the small number of identified genes. In the case of humans, only a few thousand of the complete set (30,000 to 100,000 genes) have been physically purified and characterized to any extent. Another significant limitation has been the cumbersome nature of transcription analysis. Even a large experiment on human cells would track expression of only a dozen genes, clearly an inadequate sampling for inference about so complex a control system.

Two recent technological advances have provided the means to overcome some of these limitations to examining the patterns and relationships in gene transcription. The cloning of molecules derived from mRNA transcripts in particular tissues, followed by application of high throughput sequencing to the DNA ends of the members of these libraries has yielded a catalog of expressed sequence tags (ESTs) (M. S. Boguski and G. D. Schuler, "ESTablishing a human transcript map," Nature Genetics, 10(4), 369–71, 1995). These signature sequences provide unambiguous identifiers for a large cohort of genes. At present, approximately 40,000 human genes have been "tagged" by this route, and many have been mapped to their genomic location (G. D. Schuler and M. S. Boguski, et al., "A gene map of the human genome," Science, 274(5287), 540–6, 1996).

Additionally, the clones from which these sequences were derived provide analytical reagents which can be used in the quantitation of transcripts from biological samples. The nucleic acid polymers, DNA and RNA, are biologically synthesized in a copying reaction in which one polymer serves as a template for the synthesis of an opposing strand which is termed its complement. Even after separation from each other, these strands can be induced to pair quite specifically with each other to form a very tight molecular complex, a process called hybridization. This specific binding is the basis of most analytical procedures for quantitating the presence of a particular species of nucleic acid, such as the mRNA specifying a particular protein gene product. Micro-array technology, a recent hybridization-based process that allows simultaneous quantitation of many nucleic acid species, has been described (M. Schena, D. Shalon, R. W. Davis, and P. O. Brown, "Quantitative monitoring of gene expression patterns with a complementary DNA microarray," Science, 270(5235), 467–70, 1995; J. DeRisi, L. Penland, P. O. Brown, M. L. Bittner, P. S. Meltzer, M. Ray, Y. Chen, Y. A. Su, and J. M. Trent, "Use of a cDNA microarray to analyse gene expression patterns in human cancer," Nature Genetics, 14(4), 457–60 ("DeRisi"), 1996; M. Schena, D. Shalon, R. Heller, A. Chai, P. O. Brown, and R. W. Davis, "Parallel human genome analysis: microarray-based expression monitoring of 1000 genes," Proc. Natl. Acad. Sci. USA., 93(20), 10614–9, 1996). This technique combines robotic spotting of small amounts of individual, pure nucleic acid species on a glass surface, hybridization to this array with multiple fluorescently labeled nucleic acids, and detection and quantitation of the resulting fluor tagged hybrids with a scanning confocal microscope. When used to detect transcripts, a particular RNA transcript (an mRNA) is copied into DNA (a cDNA) and this copied form of the transcript is immobilized on a glass surface. The entire complement of transcript mRNAs present in a particular cell type is extracted from cells and then a fluor-tagged cDNA representation of the extracted mRNAs is made in vitro by an enzymatic reaction termed reverse-transcription. Fluor-tagged representations of mRNA from several cell types, each tagged with a fluor emitting a different color light, are hybridized to the array of cDNAs and then fluorescence at the site of each immobilized cDNA is quantitated.

The various characteristics of this analytic scheme make it particularly useful for directly comparing the abundance of mRNAs present in two cell types. Visual inspection of such a comparison is sufficient to find genes where there is a very large differential rate of expression. A more thorough study of the changes in expression requires the ability to discern more subtle changes in expression level and the ability to determine whether observed differences are the result of random variation or whether they are likely to be meaningful changes.

SUMMARY OF THE INVENTION

The invention provides a method for analyzing expression ratios to determine significant differences in sample expressions across the gene population discernible on a micro-array. The method assumes sample expression levels are independent, levels are normally distributed, and there is a constant coefficient of variation for the entire gene set (a biochemical consequence of the mechanics of transcript production). Using these assumptions, the method derives the probability distribution of the ratio, finds the maximum-likelihood estimator for the distribution, and employs an iterative procedure for signal calibration.

With this approach, a computer-implemented method can process a single image and identify outliers. Our implementation of this method measures expression levels in digitized micro-array images. In a preprocessing phase, a non-parametric statistical technique extracts cDNA sites on the slide. The method then analyzes the expression ratio using a confidence interval and hypothesis test to quantify the significance of differences in expression ratio.

BRIEF DESCRIPTION OF THE DRAWINGS

The file of this patent application contains at least one drawing executed in color. Copies of this patent with color drawings will be provided by the Patent and Trademark Office upon request and payment of the necessary fee.

FIG. 5 is a graph of ratio density functions for c=0.05, 0.1, and 0.2, where c represents the coefficient of variation of the ratio density functions.

DETAILED DESCRIPTION

Capturing the cDNA Micro-Array Image

Figure 1:
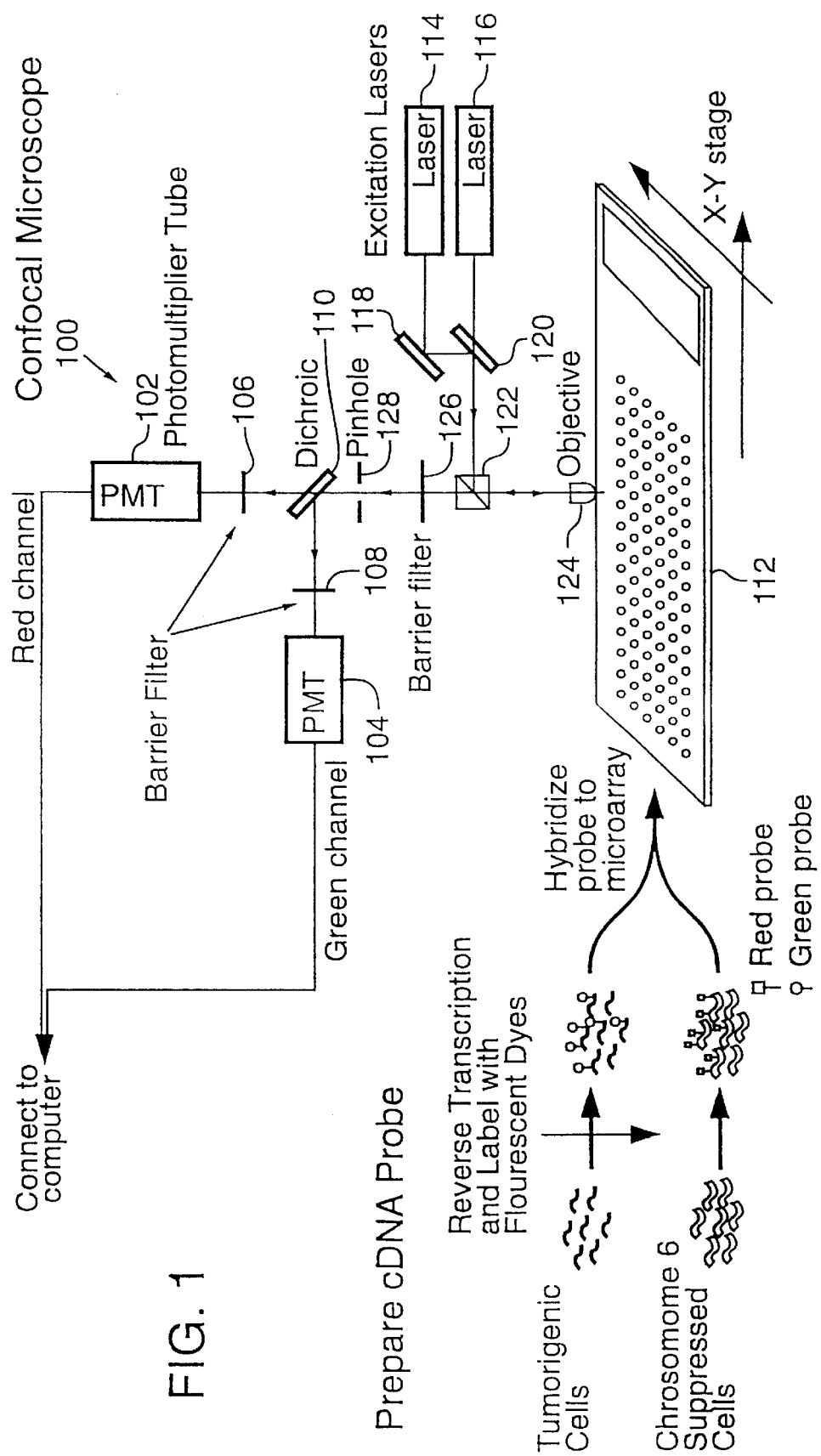
FIG. 1 is a diagram illustrating a micro-array system used to compare the abundance of mRNAs present in two cell types.

FIG. 1 is a diagram illustrating a system for capturing a cDNA micro-array image. The micro-array system employs a confocal microscope (100) to scan a micro-array image into a computer. The system has two or more color channels to detect expression levels of color-tagged cell types. Each color channel includes a photomultiplier tube (PMT 102, 104) and barrier filter (106, 108). A dichroic (110) splits the light reflected from a micro-array (112) into the channels. To generate this light, excitation lasers (114, 116) provide a light source that is directed to the surface of the micro-array (112) via optical elements (118, 120 and 122) and objective (124). To capture a digital image of the micro-array (112) in the computer, the confocal microscope scans across the micro-array in a predetermined pattern. The light reflected from the micro-array as the microscope scans over it passes through the objective (124) and beam splitter (122) to a barrier filter (126). A portion of this light passes through pinhole (128) to the dichroic (110), which splits it into two channels. The resulting color intensity signals for each channel are digitized and stored per discrete image element (referred to as a pixel) in a digital color image.

Figure 2:
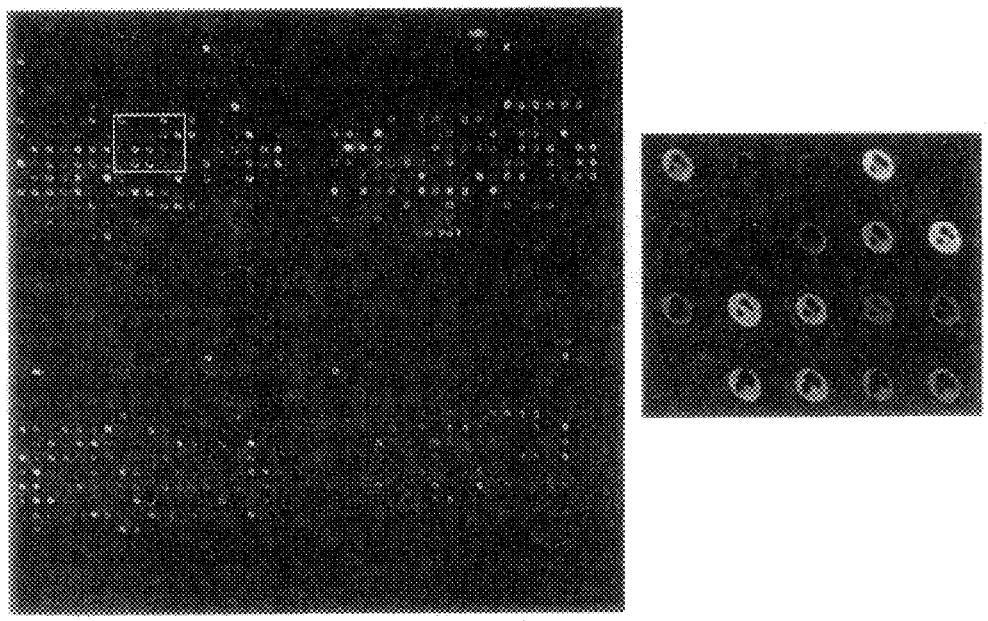
FIG. 2 is an example of a cDNA micro-array image created using the system shown in FIG. 1.

This particular system was used in an experiment to compare the abundance of mRNAs present in two cell types. In this experiment, an array of cDNAs was hybridized with a green fluor-tagged representation of mRNAs extracted from a tumorigenic melanoma cell line (UACC-903) and a red fluor-tagged representation of mRNAs from a non-tumorigenic derivative of the original cell line (UACC-903 +6). Monochrome images of the fluorescent intensity observed for each of the fluors are then combined by placing each image in the appropriate color channel of an RGB image, as shown in FIG. 2. In this composite image, one can visualize the differential expression of genes in the two cell lines. Intense red fluorescence at a spot indicates a high level of expression of that gene in the non-tumorigenic cell line with little expression of the same gene in the tumorigenic parent. Conversely, intense green fluorescence at spot indicates high expression of that gene in the tumorigenic line, with little expression in the non-tumorigenic daughter line. When both cell lines express a gene at similar levels, the observed array spot is yellow.

The experiment illustrated above represents only one example of an application of the ratio-based method for analyzing expression levels. In addition to color intensity values, it is also possible to use other ways of labeling probes and then measuring expression levels at target sites. Examples of other labeling techniques include chemifluorescent and radioactive labeling. It is also possible to analyze expression levels of more than two probes in the ratio-based method by selecting one of the probes as a reference.

The following section describes a technique for segmenting target sites in a micro-array image. This technique identifies pixels within a target patch that form a target site. The objective is to identify pixel locations where hybridization has occurred, and to distinguish such locations from the background and noise. These pixel locations can then be used to estimate expression levels more accurately at the site. While the segmentation is adapted for analyzing color intensity values of an image, it can also be adapted to other signal intensity values. Other segmentation methods may be used in the alternative.

Image Processing and Mann-Whitney Segmentation

Assuming DNA products from two samples have equal probability to hybridize to the target, intensity measurement is a function of the quantity of the specific DNA products available within each sample. Locally (or pixelwise), the intensity measurement is also a function of the concentration of the target segments. On the scanning side, the fluorescent light intensity also depends on the power and wavelength of the laser, quantum efficiency of the photo-multiplier tube and efficiency of other electronic devices. The resolution of a scanned image is largely determined by processing requirements and the acquisition speed. The scanning stage imposes a calibration requirement, though it may be relaxed later. The image analysis task is to extract the average fluorescence intensity from each target site (cDNA region).

There are several fluorescent light sources from each slide: background, target, the target hybridized with sample 1 or sample 2, and (possibly) the glass surface. The average intensity within a target site is measured by the median image value on the site. This intensity serves as a measure of the total fluors emitted from the sample mRNA probes hybridized on the target site. The median is used as the average to mitigate the effect of outlying pixel values created due to noise.

Some image processing is required prior to intensity measurement. Most is quite standard and need not be described here. For instance, the image needs to be segmented into target patches but this task is straightforward since the robot positions the cDNA targets in a predetermined manner. Because the number of pixels in the target site is limited, both smoothing and sharpening filters need to be avoided.

Figure 3:
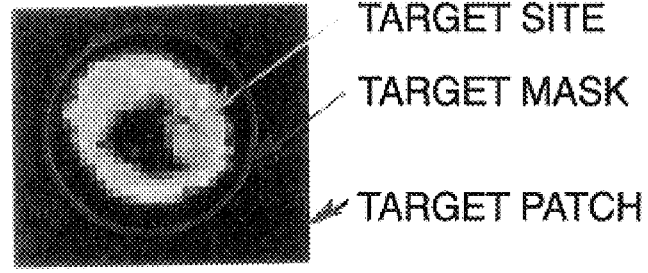
FIG. 3 is a diagram illustrating an example of a target patch, a target mask, and a target site in a cDNA micro-array image.

The difficult image processing task is to identify the target site within the target patch (see FIG. 3). Each target site is somewhat annular owing to how the robot finger places the cDNA on the slide and how the slide is treated; however, there is variability in this placement (within the patch) from image to image and from target to target. This variability can be so great that the target region is simply a collection of subregions within the nominal circular target region. This instability in the target region is manifested in the irregular way the mRNA is hybridized to the target and the consequent irregular brightness pattern (created by the fluors) within the target site. It is important that mRNA intensity be measured over these fluor regions because only they correspond to probe-hybridized-to-target areas. Conventional adaptive thresholding segmentation techniques are unsatisfactory when the signal is weak because there is no marked transition between foreground and background. Standard morphological methods also fail because for weak signals there is no consistent shape information for the target area.

To overcome these difficulties we propose a pixel selection method based on the Mann-Whitney test. There are three key points associated with the proposed Mann-Whitney approach: (1) it associates a confidence level to every intensity measurement based on the significance level of the test and, if desired, it enables multiple readouts at different confidence levels, (2) it meets the real-time requirement of the system, and (3) it is a distribution-free test, thereby eliminating the need for a normality assumptions.

We briefly describe the Mann-Whitney test as employed herein. Suppose $X_1, X_2, \ldots, X_n$ and $Y_1, Y_2, \ldots, Y_m$ are independent samples arising from two random variables X and Y possessing means $\mu_X$ and $\mu_Y$, respectively. The rank-sum statistic W, which is the sum of the ranks of all X samples in the combined ordered sequence of the X and Y samples, is used to test the null hypothesis, $$H_0: \mu_{X-\mu Y}=0 \qquad (1)$$

$$H_1: \mu_{X-\mu Y}>0$$

The Mann-Whitney criterion reveals the relation between the positions of the X and Y positions in the combined ordered sequence. Rejection of $H_0$ occurs when $W \geq w_{\alpha, n, m}$, the critical value corresponding to the significance level $\alpha$.

Figure 4A:
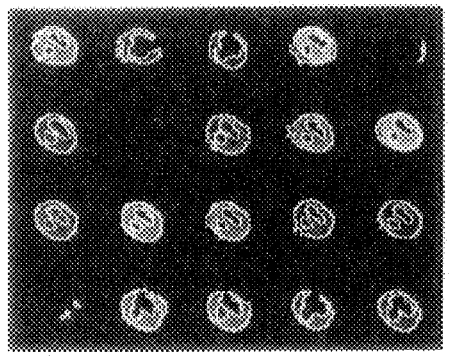
FIGS. 4A and 4B illustrate target detection results at different significant levels.
Figure 4B:
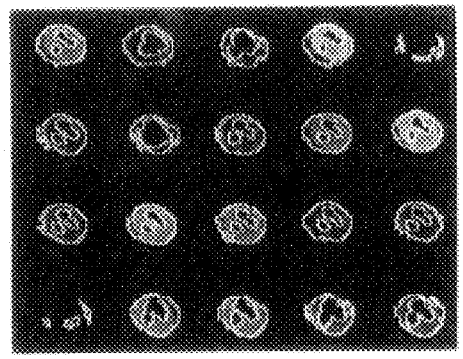

A target site is segmented from the target patch according to the following procedure. A predefined target mask is used to identify a portion of the target patch that contains the target site. The target mask is based on the geometry of the potential target area and can be constructed from specially tagged targets or other strong targets (e.g., the target mask is obtained by finding all strong targets, aligning them together, averaging and then thresholding). We randomly pick 8 sample pixels from the known background (outside the target mask) as $Y_1, Y_2, \ldots Y_8$, and select the lowest 8 samples from within the target mask as $X_1, X_2, \ldots X_8$. The rank-sum statistic W is calculated and, for a given significance level $\alpha$, compared to $w_{\alpha,8,8}$. We choose 8 samples here for both foreground and background because the Mann-Whitney statistic is approximately normal when $m=n \geq 8$. If the null hypothesis is not rejected, then we discard some predetermined number (perhaps only 1) of the 8 samples from the potential target region and select the lowest 8 remaining samples from the region. The Mann-Whitney test is repeated until the null hypothesis is rejected. When $H_0$ is rejected, the target site is taken to be the 8 pixels causing the rejection together with all pixels in the target mask whose values are greater than or equal to the minimum value of the eight. The resulting site is said to be a target site of significance level $\alpha$. If the null hypothesis is never rejected, then it is concluded that there is no appreciable probe at the target site. Furthermore, one can require that the Mann-Whitney target site contain at minimum some number of pixels for the target site to be considered valid and measured for fluor intensity. FIGS. 4a and 4b show the detection results of target sites at $\alpha=0.0001$ and $\alpha=0.05$, respectively, where detected site boundaries are superimposed with original images. Once a target site is determined, gene expression is measured by the median of the target site minus the median of the background area (outside the target mask area).

After segmenting the target site from the image data, the ratio of the expression levels at the site are computed by computing a ratio of the red intensity average and the green intensity average for pixel locations in the target site. The average of the red and green signals may be computed as the mean or median of the respective intensity values for each color. The next phase then analyzes the ratio distribution of the target sites.

Probability Density Function of Ratio Parameters

Having extracted the target site, we now use another computer program that uses the expression ratio to determine whether or not gene expression differs significantly for the red and green samples. Equal distributions for red and green values lead to a red/green ratio close to 1 and significantly unequal distributions lead to a red/green ratio significantly different from 1. In examining expression ratios, two points need to be taken into consideration. First, even if red and green measurements are identically distributed, the mean of the ratio distribution will not be 1; second, the hypothesis test needs to be performed on expression levels from a single micro-array. A salient factor in using expression ratios rather than expression differences is that gene expression levels are determined by intrinsic properties of each gene, which means that expression-level differences vary widely between genes regardless of the truth of the null hypothesis. Therefore, it is inappropriate to pool gene-expression difference statistics across the micro-array. Labeling the red and green micro-array values for the genes by $R_1, R_2, \ldots, R_n$ and $G_1, G_2, \ldots, G_n$, respectively, the desired hypothesis test is $$H_0: \mu_{R_k} = \mu_{G_k} \qquad (2)$$

$$H_1: \mu_{R_k} \neq \mu_{G_k}$$

using the test statistic $T_k = R_k/G_k$. This requires finding a critical region for $T_k$, recognizing that the mean of $T_k$ under the null hypothesis is not 1.

It is well-known that working with ratio distributions can be problematic and recent research on the matter is generally confined to normality study of the ratio distribution, and numerical calculations. However, as we now discuss, a special situation arises for gene expression that permits a more detailed statistical analysis, as well as hypothesis tests and confidence intervals based on a single micro-array.

While it would be possible to gather data on the routine level of expression for each specific gene in each specific tissue, this would be a very difficult undertaking. The method currently requires substantial quantities of mRNA (and thus tissue) for each determination. Extending the studies to pathological situations would further complicate the ability to gather material for replicates, since it will initially be necessary to assume diseases with complex molecular etiologies may have many forms, making pooling of samples from different individuals counterproductive. The most practical and informative version of an assay of this type would be achieved if information on the variance of all or most of the genes in a sample could be used to derive a statistically sound measurement of variance for each individual transcript. Fortunately, it appears that the biology of transcription makes such an approach possible.

A transcript's abundance at a given time is governed by the current rates of production and degradation of that transcript. As would be expected of a system faced with routine generation and destruction of these information intermediates, the processes which produce and destroy transcripts rely on common, core enzymatic machinery (polymerases and nucleases) whose specificity of activity is modulated by accessory proteins that bind to the core enzymes, the nucleic acid sites of action or both. As might also be expected of a system that must constantly synthesize and hydrolyze tens of thousands of molecules, molecular interactions are based on very similar intermolecular affinities. Nimbleness at this scale requires that the core machinery operate without too much bias, so that no single or small class of transcripts consumes too large a share of the machinery's capacity. This type of bulk processing is thus predicted to be an approximation of a much simpler reaction, in which the level of a transcript will depend roughly on the concentration of the accessory factors driving its selection, and the variations for any particular transcript would be expected to be normally distributed and constant (as a fraction of abundance) relative to most of the other transcripts. Such assumptions on the variances produce a special situation that can be exploited to great advantage, allowing the use of the variation data from all transcripts surveyed to be pooled to estimate the global variation of transcript synthesis and destruction. An important caveat to this hypothesis is that transcripts present at extremely high or extremely low levels could require a different method of control of synthesis/degradation and would not necessarily have variances representative of transcripts present at a common level.

Assuming there is constant coefficient of variation c for the entire gene set, $$\sigma_{R_k} = c\mu_{R_k} \qquad (3)$$

$$\sigma_{G_k} = c\mu_{G_k}$$

Under the null hypothesis $H_0$, $\mu_{R_k} = \mu_{G_k}$. Letting $\mu_k$ denote the common value, the condition of Eq. 3 becomes $\sigma_{R_k} = \sigma_{G_k} = c\mu_k$. From the experimental protocol, we assume that $R_k$ and $G_k$ are independent, identically distributed normal random variables.

If X and Y are continuous random variables, T=X/Y, and X and Y possess the joint probability density function $f_{X,Y}(x, y)$, then, the probability distribution function for T is $$F_T(t) = P(X \leq tY, Y > 0) + P(X \geq tY, Y < 0) \qquad (4)$$

$$= \int_0^\infty \left[ \int_{-\infty}^{ty} f_{X,Y}(x, y) dx \right] dy + \int_{-\infty}^0 \left[ \int_{ty}^\infty f_{X,Y}(x, y) dx \right] dy$$

For X and Y independent, differentiation yields the probability density function for T as $$f_T(t) = \int_0^\infty y f_{X,Y}(ty, y) dy - \int_{-\infty}^0 y f_{X,Y}(ty, y) dy \qquad (5)$$

$$= \int_0^\infty y f_X(ty) f_Y(y) dy - \int_{-\infty}^0 y f_X(ty) f_Y(y) dy$$

where the second equality follows from independence.

We apply Eq. 5 under the normality, independence, and constant-coefficient-of-variation conditions. Since micro-array intensity measurements are positive, densities for both red and green values are assumed to be 0 for negative arguments. The error created by the simultaneous normality and positive-value assumptions is negligible because measurement intensities are sufficiently positive to render the portions of the left distribution tails falling to the left of the y axis negligible. Letting $T_k = R_k/G_k$, $$f_{T_k}(t) = \int_0^\infty g f_{R_k}(tg) f_{G_k}(g) dg - \int_{-\infty}^0 g f_{R_k}(tg) f_{G_k}(g) dg \qquad (6)$$

$$= \int_0^\infty \frac{1}{\sigma_{R_k} \sqrt{2\pi}} e^{-\frac{(tg - \mu_{R_k})^2}{2\sigma_{R_k}^2}} \frac{1}{\sigma_{G_k} \sqrt{2\pi}} e^{-\frac{(g - \mu_{G_k})^2}{2\sigma_{G_k}^2}} g \, dg$$

$$= \frac{1}{2\pi c^2} \int_0^\infty e^{-\frac{(tu-1)^2}{2c^2}} e^{-\frac{(u-1)^2}{2c^2}} u \, du$$

where the second equality follows from the positive-value assumption and the third from Eq. 3 and the substitution $g/\mu_k = u$. Note that the density for $T_k$ is independent of k. This property is not merely a consequence of Eq. 3, but depends on normality.

The integration of Eq. 6 yields a solution that is given by the standard error equation. Notice that the second exponential in the integrand is similar to the normal density function with $\mu=1$ and $\sigma=c$. When c is small (less than 0.3), the second exponential is close to 0 for u<0. Therefore, by extending the integration to $-\infty$, we have the approximation $$f_{T_k}(t) \approx \frac{1}{2\pi c^2} \int_{-\infty}^{\infty} e^{-\frac{(tu-1)^2}{2c^2}} e^{-\frac{(u-1)^2}{2c^2}} u du \qquad (7)$$

$$= \frac{(1+t)\sqrt{1+t^2}}{c(1+t^2)^2 \sqrt{2\pi}} e^{-\frac{(t-1)^2}{2c^2(1+t^2)}}$$

The approximation error of Eq. 7 can be numerically evaluated. For example, given c=0.3, at t=1.0 the approximation error between Eqs. 6 and 7 is $4.8 \times 10^{-8}$, and at t=3.0 the error is $1.2 \times 10^{-8}$. FIG. 5 depicts the probability density function given in Eq. 7 for c=0.05, 0.1, and 0.2. The density function of Eq. 7 is an asymmetric function and its peak is close to 1, under the null hypothesis. Since Eqs. 6 and 7 are not functions of k, we denote the density function by $f_T(t; c)$ with parameter c.

Confidence Intervals and Maximum-Likelihood Estimation

Confidence intervals can be obtained via Eq. 7. Table 1 lists the upper (right) limit and lower (left) limit of 95% confidence intervals for different c values, as well as the means and standard deviations of the corresponding distributions. As functions of c, the confidence-interval limits, mean and standard deviation can be approximated by polynomial functions $$y = a_3 c^3 + a_2 c^2 + a_1 c + a_0 \qquad (8)$$

Figure 6:
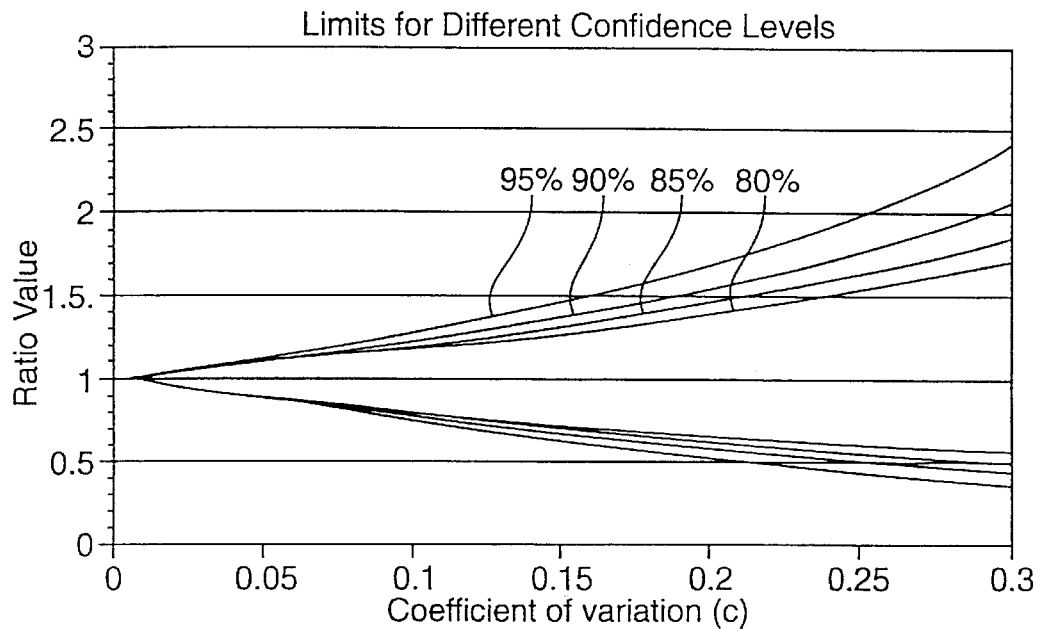
FIG. 6 is a graph illustrating upper and lower limits for different confidence levels.

Table 2 gives the appropriate polynomial coefficients for the upper limit, lower limit, mean and standard deviation. FIG. 6 provides curves for 95%, 90%, 85% and 80% confidence levels. Most results obtained here have been verified by Monte Carlo simulation. Referring back to the hypothesis test of Eq. 1, for each k, the acceptance region for the test statistic $T_k$ is the confidence interval for the appropriate value of c and the confidence level.

Typically, c needs to be estimated from the data. Using the density of Eq. 7 we can obtain a maximum-likelihood estimator for c. The likelihood function is $$L(c) = \prod_{i=1}^{n} \frac{(1+t_i)\sqrt{1+t_i^2}}{c(1+t_i^2)^2 \sqrt{2\pi}} e^{-\frac{(t_i-1)^2}{2c^2(1+t_i^2)}} \qquad (9)$$

where $t_1, t_2, \ldots, t_n$ are ratio samples taken from a single collection of expression values, for example, all ratios from the housekeeping genes in a micro-array. The maximum-likelihood criterion requires that $d[\log L(c)]/dc = 0$. Hence, the estimator for c is $$\hat{c} = \sqrt{\frac{1}{n} \sum_{i=1}^{n} \frac{(t_i - 1)^2}{(1+t_i^2)}} \qquad (10)$$

Uncalibrated Signals

Figure 7:
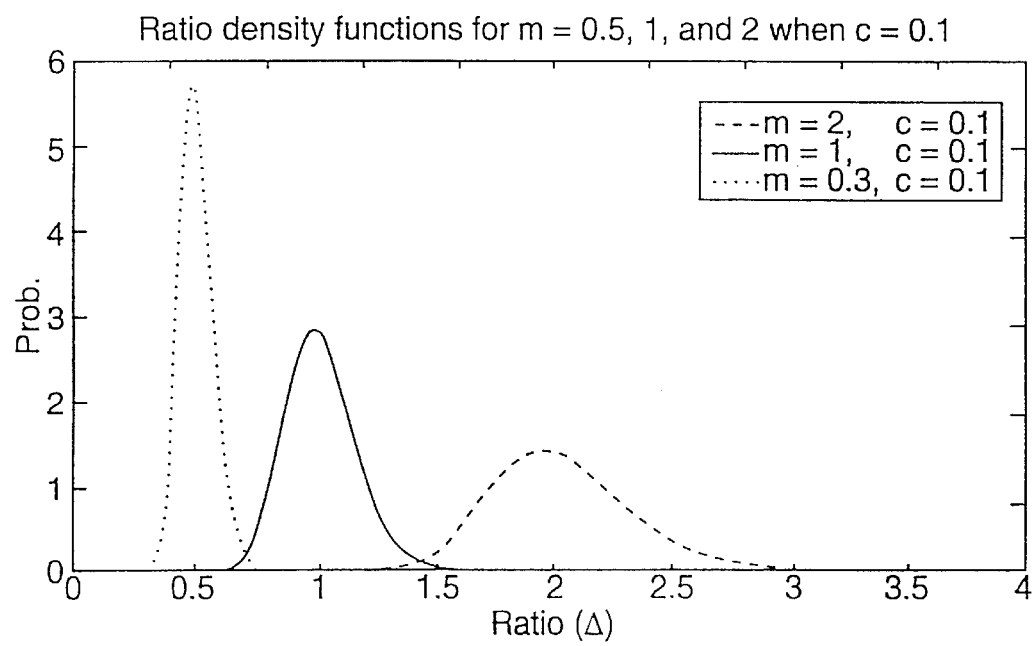
FIG. 7 is a graph illustrating ratio density functions for m=0.5, 1, and 2 when c=0.1, where m represents the gain factor relating the mean values of the red and green signals.

The null hypothesis of equal means is appropriate for calibrated signal acquisition but in practice this may not be the case. Therefore we consider the uncalibrated situation in which the means of the red and green signals are related by a constant amplification (or reduction) gain factor m, $\mu_{R_k} = m\mu_{G_k}$. If $m \geq 1$, then the red signal is stronger than the green. We can follow the same derivation as in the calibrated case except that now the ratio density has two parameters, c and m. This results in the recursive relation $$f_T(t; c, m) = \frac{1}{m} f_T(t/m, c, 1) \qquad (11)$$

where $f_T(\bullet; c, 1)$ is given by Eq. 7. FIG. 7 shows cases for m=0.5, 1, and 2 (when c=0.1). For m=0.5 we expect $R_k/G_k$ to be about 0.5, which is what FIG. 7 indicates.

In the uncalibrated setting, estimators are required for both c and m; however, a closed-form solution as in the calibrated case is precluded by reliance on the recursion of Eq. 11. Our program proceeds iteratively to obtain estimators. As shown in Table 1, the means for different c values are very close to 1 when m=1.

TABLE 1

Lower and upper limits at 95% confidence level, and other statistics of ratio density.

| Input | Output Distribution Parameters | | | | | |
|---|---|---|---|---|---|---|
| Dist. c.v. (c) | L. Limit | U. Limit | mean ($\mu$) | dev. ($\sigma$) | c.v. ($\sigma/\mu$) | peak $S_{max}$ |
| 0.01 | 0.972 | 1.026 | 1.0001 | 0.014 | 0.0141 | 0.9998 |
| 0.02 | 0.945 | 1.052 | 1.0004 | 0.028 | 0.0283 | 0.9992 |
| 0.03 | 0.919 | 1.08 | 1.0009 | 0.042 | 0.0424 | 0.9982 |
| 0.04 | 0.894 | 1.108 | 1.0016 | 0.056 | 0.0567 | 0.9968 |
| 0.05 | 0.869 | 1.137 | 1.0025 | 0.071 | 0.0710 | 0.9950 |
| 0.06 | 0.845 | 1.167 | 1.0036 | 0.085 | 0.0854 | 0.9928 |
| 0.07 | 0.822 | 1.198 | 1.0049 | 0.100 | 0.0998 | 0.9903 |
| 0.08 | 0.798 | 1.230 | 1.0065 | 0.115 | 0.1144 | 0.9873 |
| 0.09 | 0.776 | 1.263 | 1.0083 | 0.130 | 0.1291 | 0.9840 |
| 0.10 | 0.754 | 1.297 | 1.0103 | 0.145 | 0.1440 | 0.9804 |
| 0.11 | 0.732 | 1.332 | 1.0125 | 0.161 | 0.1591 | 0.9764 |
| 0.12 | 0.710 | 1.369 | 1.0150 | 0.177 | 0.1744 | 0.9720 |
| 0.13 | 0.689 | 1.407 | 1.0178 | 0.193 | 0.1900 | 0.9673 |
| 0.14 | 0.669 | 1.447 | 1.0208 | 0.210 | 0.2059 | 0.9623 |
| 0.15 | 0.648 | 1.488 | 1.0242 | 0.227 | 0.2222 | 0.9570 |
| 0.16 | 0.628 | 1.531 | 1.0278 | 0.245 | 0.2389 | 0.9514 |
| 0.17 | 0.609 | 1.576 | 1.0318 | 0.264 | 0.2561 | 0.9455 |
| 0.18 | 0.589 | 1.623 | 1.0362 | 0.283 | 0.2740 | 0.9393 |
| 0.19 | 0.570 | 1.672 | 1.0409 | 0.304 | 0.2925 | 0.9329 |
| 0.20 | 0.551 | 1.724 | 1.0460 | 0.326 | 0.3118 | 0.9262 |
| 0.21 | 0.532 | 1.778 | 1.0515 | 0.349 | 0.3319 | 0.9192 |
| 0.22 | 0.514 | 1.835 | 1.0574 | 0.372 | 0.3526 | 0.9122 |
| 0.23 | 0.495 | 1.895 | 1.0637 | 0.397 | 0.3740 | 0.9049 |
| 0.24 | 0.477 | 1.958 | 1.0702 | 0.423 | 0.3958 | 0.8974 |
| 0.25 | 0.459 | 2.026 | 1.0770 | 0.450 | 0.4178 | 0.8898 |
| 0.26 | 0.441 | 2.098 | 1.0840 | 0.477 | 0.4400 | 0.8820 |
| 0.27 | 0.424 | 2.174 | 1.0909 | 0.504 | 0.462 | 0.8740 |
| 0.28 | 0.407 | 2.257 | 1.0979 | 0.531 | 0.4840 | 0.8660 |
| 0.29 | 0.390 | 2.346 | 1.1047 | 0.558 | 0.5055 | 0.8579 |
| 0.30 | 0.373 | 2.442 | 1.1113 | 0.585 | 0.5266 | 0.8497 |

Intuitively, when two signals are approximately the same, the mode of the ratio density will be around 1. Therefore, a usual calibration practice is to move the ratio histogram mode to 1 when the red and green signals are not calibrated. This calibration procedure is not strictly correct because the peak of the ratio density changes with parameter c. To account for this effect, we first assume the population mean $\mu_0$ to be 1 and let the first approximation $m_1$ of the calibration parameter be the sample mean. The sample data is then calibrated by $m_1$. After that, Eq. 10 is used to estimate the first approximation $c_1$ of c. Estimation proceeds by iteratively repeating the procedure.

Figure 8:
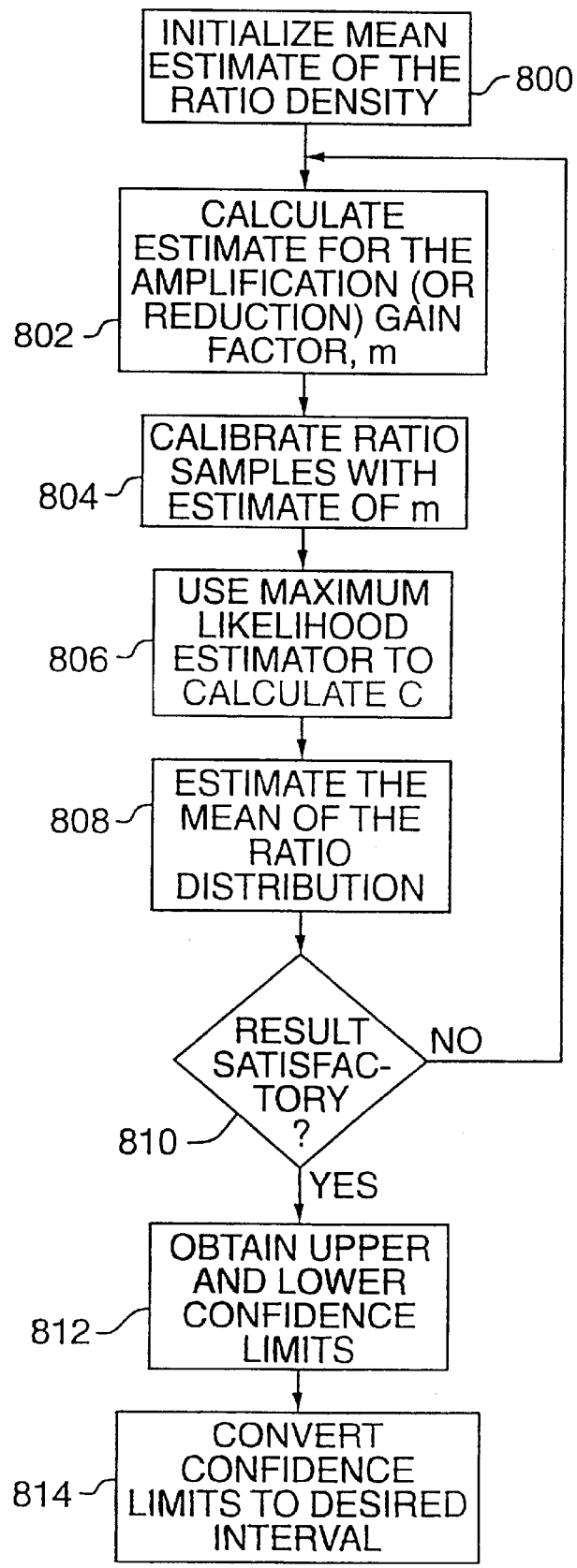
FIG. 8 is a flow diagram illustrating a method for analyzing expression ratios.

FIG. 8 is a flow diagram illustrating the steps performed by a computer program to compute ratios of expression levels. The method employed by this program proceeds as described below. The following description refers to steps in the flow diagram shown in FIG. 8 by reference numbers.

1. Initialize mean estimate $\hat{\mu}_0$ of the ratio density of Eq. 7 to be 1 (equivalent to assuming $c_0=0$). See step 800.

2. Calibrate ratio samples so that the input red and green signals are approximately equal by taking the estimator of m, say $\hat{m}_i$, to be the sample mean divided by the previous mean estimator, $$\hat{m}_i = \frac{1}{\hat{\mu}_{i-1}}\left(\frac{1}{n}\sum_{i=1}^{n} t_i\right) \qquad \text{See step 802.} \qquad (12)$$

The calibration factor is taken to be $1/\hat{m}_i$. The normalized ratio data set is $(t'_1, t'_2, \ldots, t'_i)=(t_1/\hat{m}_i, t_2/\hat{m}_i, \ldots, t_n/\hat{m}_i)$ (13) See step 804.

3. Use the maximum-likelihood estimator of Eq. 10 to calculate $\hat{c}_i$ by evaluating the estimator with the newly calibrated ratio data ($t_{i'}$, $i=1, 2, \ldots, n$). See step 806.
4. Estimate the mean $\hat{\mu}_i$ of the ratio distribution, given the new $\hat{c}_i$, by using the polynomial regression given in Table 2 ($\mu=0.364c^3+1.279c^2-0.0427c+1.001$). See step 808.
5. Repeat steps 2 through 4 until a satisfactory result is obtained. FIG. 8 illustrates this iterative process with a loop from decision block 810 back to step 802. For example, the steps could be repeated until a coefficient of variation and estimated mean of the expression ratio samples are within a threshold amount of a previously calculated coefficient of variation and estimated mean. Since the ratio mean p is close to 1 for even relatively large values of c, five iterations are usually sufficient.
6. Upper and lower confidence limits ($\theta_1, \theta_2$) can be obtained using Table 1 or 2 (Step 812), and then converting them to the desired interval ($\theta_1 \cdot \hat{m}, \theta_2 \cdot \hat{m}$) (Step 814).

TABLE 2

Parameters of fitting polynomial functions.

| Conf. Level | | $a_3$ | $a_2$ | $a_1$ | $a_0$ | goodness of fit ($R^2$) |
|---|---|---|---|---|---|---|
| 95% | Lower limit | -2.805 | 2.911 | -2.706 | 0.979 | 0.999994 |
| | Upper limit | 28.644 | -2.830 | 3.082 | 0.989 | 0.99993 |
| 99% | Lower limit | -5.002 | 4.462 | -3.496 | 0.9968 | 0.99998 |
| | Upper limit | 78.349 | -15.161 | 4.810 | 0.9648 | 0.99998 |
| | mean ($\mu$) | 0.364 | 1.279 | -0.0427 | 1.001 | 0.9997 |
| | Std. Dev. | 6.259 | 0.190 | 1.341 | 0.0022 | 0.9998 |

To verify the accuracy of the iterative method under the $H_0$ condition ($\mu_{R_k}=\mu_{G_k}$), we performed the following simulation assuming 100 red and 100 green intensity data. For $k=1, 2, \ldots, 100$, the kth red signal's (representing the kth gene expression level in sample 1) mean intensity $\mu_{R_k}$ is drawn from a uniform random process with range from 100 to 30,000 (simulating 16-bit integer range). For a given m and c value, along with the normality for both red and green signals, we generate a single datum for both the kth red and green signal, thereby obtaining a sample of the red/green ratio for each k. Simulations were done for m from 0.3 to 3 with a step of 0.1, and for c from 0.01 to 0.3 with a step of 0.01, each simulation involving the full iterative procedure. The entire simulation was repeated 30 times for each value of m and c. Average estimation errors for c and m are under 1% where error for c is defined as $|(\hat{c}-c)/c|$ and for m similarly.

Experimental Results

Consider the superimposed micro-array image from UACC-903 (red channel) and UACC-903(+6) (green channel) shown in FIG. 2. The full array contains 1,368 clone segments. A total of 88 ratio samples whose ratios are believed to be about 1 (whose gene expression levels are assumed unchanged in both cell lines), such as housekeeping genes, are listed in Appendix B. Since acquisition does not insure perfect calibration, the iterative procedure is used. The result is as follows:

m 1.1316 c 0.1727 (or 17.27%)

99% confidence interval: (0.566, 1.977)

The step by step illustration of the iterative estimation is listed in Table 3. The 99.0% confidence interval for c=0.1727 and m=1.1316 is (0.56617, 1.97684).

TABLE 3

Step by step illustration of the iterative estimation.

| Step $i$ | Sample Scaling factor | $c_i$ (Eq. 10) | $\mu_i$ (Table 2) | $m_i$ (Eq. 12) |
|---|---|---|---|---|
| initial | — | — | $\mu_0 = 1.0$ | $m_0 = 1.1697$ |
| 1 | $1/m_0$ | 0.1741 | 1.03425 | 1.1420 |
| 2 | $1/m_1$ | 0.1728 | 1.03370 | 1.1315 |
| 3 | $1/m_2$ | 0.1727 | 1.03365 | 1.1316 |
| 4 | $1/m_3$ | 0.1727 | Stop! | — |

Based on this interval, 92 ratio samples are found to be significant. Of these, 70 were found to be significant using the inappropriately narrow confidence interval reported by DeRisi (see Appendix C.

TABLE 4

Named genes, shown in decreasing ratio order, are additional genes found to have different expression levels in a chromosome 6 suppressed melanoma cell line than in its tumorigenic parent (99% confidence level). The original findings were reported by DeRisi.

| Gene Name | R/G Ratio |
|---|---|
| pre-mRNA splicing factor SRp7 | 2.33 |
| casein kinase I delta | 2.33 |
| MAC25 | 2.32 |
| endothelin-1 (EDN1) | 2.30 |
| B12 protein | 2.25 |
| RSU-1/RSP-1 | 2.25 |
| Id1 | 2.24 |
| similar to induced myeloid leukemia cell differentiation protein | 2.22 |
| male-enhanced antigen mRNA (Mea) | 2.20 |
| PP15 (placental protein 15) | 2.20 |
| vascular endothelial GF | 2.18 |
| calphobindin II | 2.18 |
| similar to mouse transplantation antigen p35B | 2.15 |
| 22kDa smooth muscle protein (SM22) | 2.15 |
| alternative guanine nucleotide-binding regulatory protein (G) | 2.13 |
| nuclear autoantigen GS2NA | 2.13 |
| cadherin-associated protein-related (cap-r) | 2.13 |
| mitochondrial phosphate carrier protein | 2.12 |
| alpha NAC | 2.10 |
| thymopoietin beta | 2.08 |
| B lymphocyte serine/threonine protein kinase | 2.07 |
| platelet alpha SNAP | 2.06 |
| lamin B2 (LAMB2) | 2.06 |
| CMAR | 2.06 |
| inosine-5'-monophosphate dehydrogenase (IMP) | 2.02 |
| I-Rel | 1.99 |
| DNA-binding protein (CROC-1A) | 1.99 |
| polyA binding protein | 1.98 |
| bcr (break point cluster gene) | 0.57 |
| mitotic feedback control protein Madp2 homolog | 0.55 |
| protein-tyrosine phosphatase | 0.55 |
| Human poly(ADP-ribose) synthetase | 0.53 |

Table 4 lists the ones missed by the confidence limits reported by DeRisi. Some of the newly found significant changes are biologically interesting and further bolster general impressions resulting from the original cohort of genes showing significant changes. Two further examples of the tendency of the chromosome 6 suppressed line toward increased expression of genes associated with differentiation are the myeloid leukemia cell differentiation protein (mcl1) and the cell adhesion regulator protein (CAR/CMAR). Increased expression of the mcl1 gene has been found to be a very early indicator of induced differentiation in cancer cells. See A. Umezawa, T. Maruyama, et al, "Induction of mcl1/EAT, Bcl-2 related gene, by retinoic acid or heat shock in the human embryonal carcinoma cells, NCR-G3," Cell Structure Function, 21(2), 132–50, (1996); and T. Yang, H. L. Buchan, et al. "MCL-1, a member of the BLC-2 family, is induced rapidly in response to signals for cell differentiation or death, but not to signals for cell proliferation," J. Cell Physiology, 166(3), 523–36 (1996).

Increased expression of the CAR gene has been correlated with reduced spontaneous metastatic potential in the HT-29 (human adenocarcinoma) cell line, presumably due to a greater repertoire of integrins with increased adherence of the cells to the extracellular matrix. See H. Yamamoto, F. Itoh, et al. "Inverse association of cell adhesion regulator messenger RNA expression with metastasis in human colorectal cancer," Cancer Research, 56(15), 3605–9, (1996).

In addition to the tendency toward expression of genes associated with differentiation, changes are observed that suggest that the suppressed cells are more capable of modulating oncogene activity. In addition to the strong increase in p21 expression previously seen, significant increase in the expression of the ras suppressor Rsu-1 is observed. Rsu-1 has been shown to be a potent inhibitor of Jun kinase activation. L. Masuelli and M. L. Cutler "Increased expression of the Ras suppressor Rsu-1 enhances Erk-2 activation and inhibits Jun kinase activation," Molecular Cell Biology, 16(10), 5466–76, (1996).

Adaptive Confidence Interval

The confidence interval derived from ratio distribution, defined by Eq. 7 is a fixed interval regardless of the gene expression level. Taking into account the background signal, the expression intensity measurement may be expressed as:

$$R_k = (SR_k + BR_k) - \mu_{BR_k} \quad (12)$$

where $SR_k$ is the expression intensity of gene k to be measured, $BR_k$ is the fluorescent background level and $\mu_{BR_k}$ is the mean background level. Since the measurable quantities are the signal with background ($SR_k + BR_k$) and the background itself, $R_k$ is reported as the background subtracted expression intensity, or the estimator of the kth gene expression intensity. $R_k$ is then used for ratio calculation $T = R_k/G_k$ in Eqs. 2 to 7. Taking the expectation of Eq. 12, we have:

$$\mu_{R_k} = E[R_k] = E[(SR_k + BR_k) - \mu_k] = \mu_{SR_k} + \mu_{BR_k} - \mu_{BR_k} = \mu_{SR_k} \quad (13)$$

Equation 13 indicates the ideal situation upon which the hypothesis test Eq. 2 is based. However, the same assumption does not yield Eq. 3 when the standard deviation of the background level is not zero or the signal intensity is weak. We have, $$\sigma_{R_k}^2 = \sigma_{SR_k}^2 + \sigma_{BR_k}^2 = (c\,\mu_{SR_k})^2 + \sigma_{BR_k}^2, \quad \text{and} \quad (14)$$

$$(c'_{R_k})^2 = (\sigma_{R_k}/\mu_{SR_k})^2 = c^2 + \sigma_{BR_k}^2/\mu_{SR_k}^2 = c^2 + \left(\frac{1}{SNR}\right)^2$$

where c is the coefficient of variation of the gene expression level which is a constant described by Eq. 3. $c_{R_k}$ is the coefficient of variation of the reported expression intensity for gene k from the red channel. $\sigma_{BR_k}/\sigma_{SR_k}$ is defined as the inverse of Signal-to-Noise Ratio ($SNR = \mu_{SR_k}/\sigma_{BR_k}$), and we also assume the signal process is independent of the background process. When SNR>>1, $c_{R_k} \approx c$. In the case where the signal is weak, $c_{R_k}$ is greatly altered or different from $c_{G_k}$ (due to the difference of background levels from red and green channels) such that Eq. 7 is no longer valid. When the expression signal is weaker, the spread is larger.

When the background level is taken into the consideration as given in Eq. 12, the expression ratio can be written as, $$T_k = \frac{R_k}{G_k} = \frac{(SR_k + BR_k) - \mu_{BR_k}}{(SG_k + BG_k) - \mu_{BG_k}} \quad (15)$$

where $R_k$ and $G_k$ are the expression intensities measured from red and green channels, respectively. If housekeeping genes are employed in ratio analysis, we have $SR_k = SG_k$. $BR_k$ and $BG_k$ are the background intensities from red and green channels, respectively. Due to the result given in Eq. 14, the condition given in Eq. 3 is no longer satisfied, and the distribution of ratio $T_k$ does not assume a simple analytical form. To fully understand the property of ratio T, we choose the Monte Carlo method where, $$T = \frac{N(p, \sigma_p) + N(\mu_{BR}, \sigma_{BR}) - \mu_{BR}}{N(p, \sigma_p) + N(\mu_{BG}, \sigma_{BG}) - \mu_{BG}} \quad (16)$$

We assume the expression intensity possesses a normal distribution $N(\mu, \sigma)$ with mean expression intensity $p = \mu_{SR_k} = \mu_{SG_k}$, given the null hypothesis where only the housekeeping genes are used. We further assume that the coefficient of variation of the actual gene expression intensity is a constant c, thus, $\sigma_p = c \cdot p$. Also, let the background process be an independent process with normal distribution of mean $\mu_{BR}$ and standard deviation $\sigma_{BR}$ for the red channel background level. The green channel background level can be similarly defined. To simplify the notation, we omit k in Eq. 16. It is important to point out that: 1) the confidence interval diverges when the SNR is small (the expression intensity is small relative to the background), 2) when SNR>10, the confidence interval starts to converge to the previously derived result given by Eq. 7, and 3) when SNR=0, the confidence interval is limited by the ratio distribution of background levels from red and green channels. It can also be demonstrated that when two background levels are not the same, the upper and lower bounds are not symmetric.

For a given microarray slide, we can use the average of the local background intensity and its standard deviation as an estimate of $\mu_{BR}$ and $\mu_{BR}$, respectively. The background statistics for the green channel can be similarly obtained. The coefficient of variation, c, of the expression intensity is derived from ratio analysis given by Eq. 10 (or an improved version of Eq. 10 is given in Eq. 22) when a set of housekeeping genes is identified. The Monte Carlo simulation of Eq. 16 is then performed and the adaptive confidence interval can be assigned to every gene. Depending on the image analysis algorithm, if the local background is extracted instead of the global background, the Monte Carlo simulation may need to be performed at each gene location since the background process can be very different from place to place.

Quality Weight of Ratios

For a given cDNA target, we would like to use the information obtained from the target detection algorithm to derive a measurement quality metric w which takes a value from 1 (highest measurement quality) to 0 (lowest measurement quality). A typical weighting factor can be defined as, $$w = w_a w_p w_b \quad (17)$$

where $$w_a = \begin{cases} 0, & a < s_b = \max(\mu_a - 3\sigma_a, 0) \\ \dfrac{a - s_b}{s_a - s_b}, & s_b < a \le s_a = \max(\mu_a - 2\sigma_a, a_{10\%}) \\ 1, & \text{otherwise} \end{cases} \quad (18)$$

$$w_p = \begin{cases} \max\left(\dfrac{R_k}{6\sigma_{BR_k}}, \dfrac{G_k}{6\sigma_{BG_k}}\right) = \dfrac{\max(SNR_{R_k}, SNR_{G_k})}{6}, & \max(SNR_{R_k}, SNR_{G_k}) < 6 \\ 1, & \text{otherwise} \end{cases} \quad (19)$$

$$w_{BR} = \begin{cases} 1, & BR_k < \mu_{BR} + 3\sigma_{BR} \\ \dfrac{(\mu_{BR} + 6\sigma_{BR}) - BR_k}{3\sigma_{BR}}, & \mu_{BR} + 3\sigma_{BR} \le BR_k < \mu_{BR} + 6\sigma_{BR} \\ 0, & BR_k \ge \mu_{BR} + 6\sigma_{BR} \end{cases} \quad (20)$$

$$w_b = \min(w_{BR}, w_{BG}) \quad (21)$$

In Eq. 18, a is the detected area of cDNA target site, with mean and standard deviation of $\mu_a$ and $\sigma_a$, respectively, and $a_{10\%}$ the 10 percentile location. In Eqs. 19 and 20, $\mu_{BR_k}$ and $\sigma_{BR_k}$ are the local background mean intensity and its standard deviation, respectively, and, $\mu_{BR}$ and $\sigma_{BR}$ (irrelevant to the position of gene k) are the global background mean intensity and its standard deviation, respectively. In Eq. 21, $w_{BG}$ is similarly defined as in Eq. 20. A weight w smaller than 1.0 indicates the following quality problems: 1) the detected target area is too small, 2) the signals from both channels are weak (within the variation of background level), and 3) the local background is greatly deviated from the global background level.

Using one or more of these weighting factors ($w_a$ $w_p$ $w_b$), we can add a new condition for ratio outliers: 1) the ratio must be outside the confidence interval, and 2) the ratio must have a higher quality weight (w≈1).

One of the direct applications of the quality weight for each cDNA target is the ratio parameter estimator given by Eq. 10, which can be re-written as, $$c = \sqrt{\sum_{i=1}^{n} w_i \dfrac{(t_i - 1)^2}{(t_i^2 + 1)} \Big/ \sum_{i=1}^{n} w_i} \quad (22)$$

Equation 22 provides a robust estimator for c even when a strong noise is presented. Additionally, there is no need to add some data filtering steps before evaluating Eq. 22, resulting in a stable c free of any further data filtering.

The quality weight is useful for down-stream data analysis tasks, such as the similarity measure for gene expression profile analysis. A typical similarity measure is the correlation coefficient, which can be easily modified by introducing the weight into the calculation as, $$\rho_{xy} = \dfrac{\sum_{i=1}^{n} w_{x_i} w_{y_i} (x_i - \mu_x)(y_i - \mu_y) \Big/ \sum_{i=1}^{n} w_{x_i} w_{y_i}}{\left(\sum_{i=1}^{n} w_{x_i}(x_i - \mu_x)^2 \sum_{i=1}^{n} w_{y_i}(x_i - \mu_x)^2 \Big/ \sum_{i=1}^{n} w_{x_i} \sum_{i=1}^{n} w_{y_i}\right)^{1/2}} \quad (23)$$

where $x_i$ and $y_i$ is the log-transformed ratio for gene x and y of experiment i.

Operating Environment for the Invention

Figure 9:
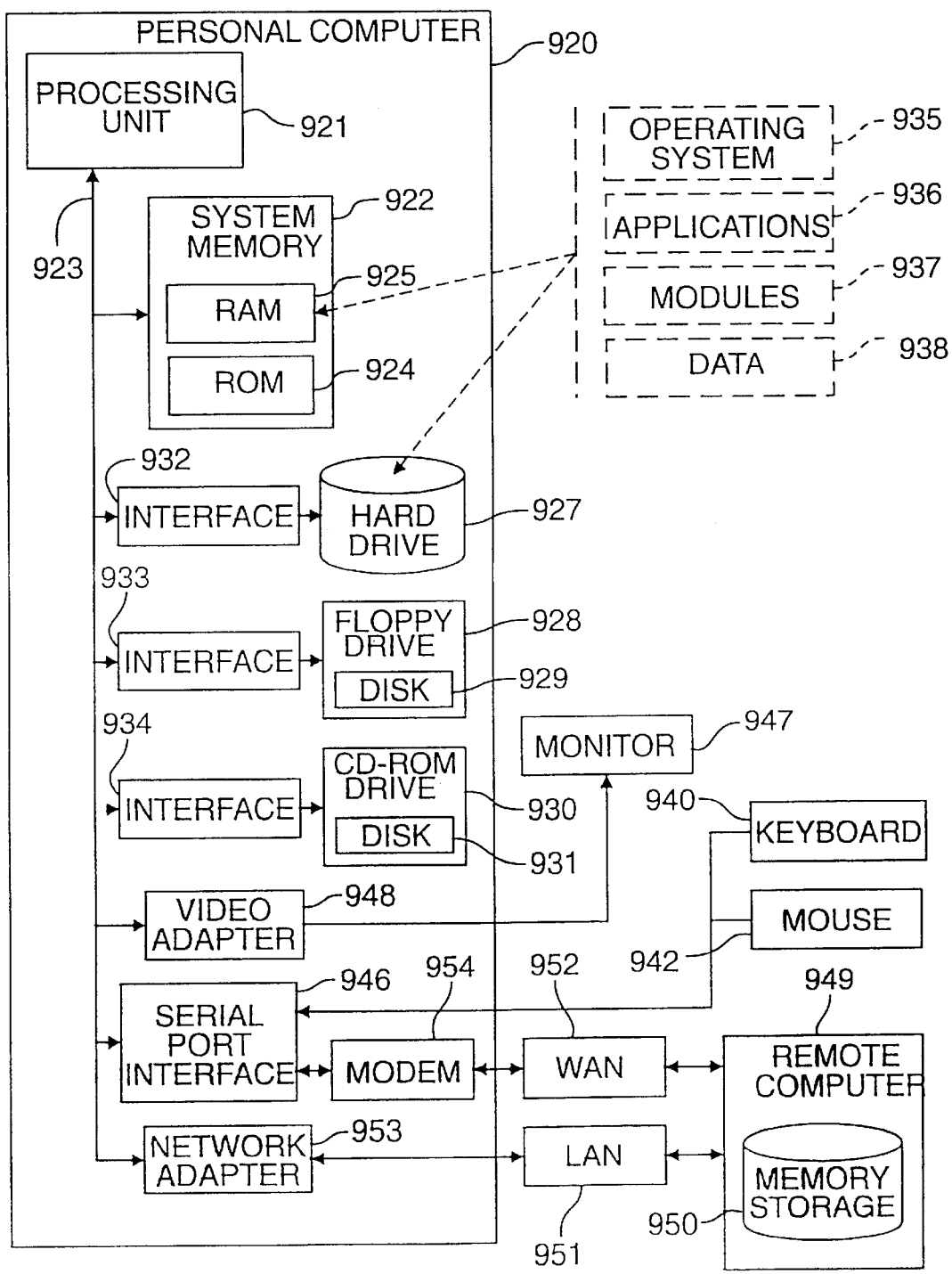
FIG. 9 is a block diagram illustrating a computer system which serves as an operating environment for an implementation of the invention.

FIG. 9 and the following discussion are intended to provide a brief, general description of a suitable computing environment for the computer programs described above. The method for analyzing expression ratios is implemented in computer-executable instructions organized in program modules. The program modules include the routines, programs, objects, components, and data structures that perform the tasks and implement the data types described above.

While FIG. 9 shows a typical configuration of a desktop computer, the invention may be implemented in other computer system configurations, including multiprocessor systems, microprocessor-based or programmable consumer electronics, minicomputers, mainframe computers, and the like. The invention may also be used in distributed computing environments where tasks are performed by remote processing devices that are linked through a communications network. In a distributed computing environment, program modules may be located in both local and remote memory storage devices.

The computer system shown in FIG. 9 includes a personal computer 920, including a processing unit 921, a system memory 922, and a system bus 923 that interconnects various system components including the system memory to the processing unit 921. The system bus may comprise any of several types of bus structures including a memory bus or memory controller, a peripheral bus, and a local bus using a bus architecture such as PCI, VESA, Microchannel (MCA), ISA and EISA, to name a few. The system memory includes read only memory (ROM) 924 and random access memory (RAM) 925. A basic input/output system 926 (BIOS), containing the basic routines that help to transfer information between elements within the personal computer 920, such as during start-up, is stored in ROM 924. The personal computer 920 further includes a hard disk drive 927, a magnetic disk drive 928, e.g., to read from or write to a removable disk 929, and an optical disk drive 930, e.g., for reading a CD-ROM disk 931 or to read from or write to other optical media. The hard disk drive 927, magnetic disk drive 928, and optical disk drive 930 are connected to the system bus 923 by a hard disk drive interface 932, a magnetic disk drive interface 933, and an optical drive interface 934, respectively. The drives and their associated computer-readable media provide nonvolatile storage of data, data structures, computer-executable instructions (program code such as dynamic link libraries, and executable files), etc. for the personal computer 920. Although the description of computer-readable media above refers to a hard disk, a removable magnetic disk and a CD, it can also include other types of media that are readable by a computer, such as magnetic cassettes, flash memory cards, digital video disks, Bernoulli cartridges, and the like.

A number of program modules may be stored in the drives and RAM 925, including an operating system 935, one or more application programs 936, other program modules 937, and program data 938. A user may enter commands and information into the personal computer 920 through a keyboard 940 and pointing device, such as a mouse 942. Other input devices (not shown) may include a microphone, joystick, game pad, satellite dish, scanner, or the like. These and other input devices are often connected to the processing unit 921 through a serial port interface 946 that is coupled to the system bus, but may be connected by other interfaces, such as a parallel port, game port or a universal serial bus (USB). A monitor 947 or other type of display device is also connected to the system bus 923 via an interface, such as a display controller or video adapter 948. In addition to the monitor, personal computers typically include other peripheral output devices (not shown), such as speakers and printers.

The personal computer 920 may operate in a networked environment using logical connections to one or more remote computers, such as a remote computer 949. The remote computer 949 may be a server, a router, a peer device or other common network node, and typically includes many or all of the elements described relative to the personal computer 920, although only a memory storage device has been illustrated in FIG. 9. The logical connections depicted in FIG. 9 include a local area network (LAN) 951 and a wide area network (WAN) 952. Such networking environments are commonplace in offices, enterprise-wide computer networks, intranets and the Internet.

When used in a LAN networking environment, the personal computer 920 is connected to the local network 951 through a network interface or adapter 953. When used in a WAN networking environment, the personal computer 920 typically includes a modem 954 or other means for establishing communications over the wide area network 952, such as the Internet. The modem 954, which may be internal or external, is connected to the system bus 923 via the serial port interface 946. In a networked environment, program modules depicted relative to the personal computer 920, or portions thereof, may be stored in the remote memory storage device. The network connections shown are merely examples and other means of establishing a communications link between the computers may be used.

Conclusion

Ratios are used to quantify gene-expression distinctions on a cDNA micro-array arising from different samples. Under the mathematical conditions assumed for average mRNA expression intensities, the ratio distribution has been derived, maximum-likelihood estimation characterized, and calibration achieved via an iterative algorithm. Empirically, a careful mathematical analysis of calibration and confidence limits has revealed significant gene-expression ratios that were missed with a less precise analysis.

While the above description focuses on a specific implementation of a method for quantitatively analyzing gene expression levels, the invention is not limited to this specific implementation. This analysis method generally applies to any form of detectable signals as long as the signals are (a) hybridized to the same site; and (b) proportional to the corresponding input probes. Condition (a) is important because the amount of target cDNA or its binding quality will be reflected in the detected signal intensity. When multiple probes are hybridized to the same target, they are exposed to the same condition. Condition (b) is important because it avoids competition for hybridization. In practice, the target concentration should be in great excess relative to the probes such that a disproportionate signal favoring more abundant species is eliminated.

More than two probes can be hybridized to the same slide as long as the target cDNA concentration is sufficiently large that no competition for hybridization sites is observed and the signal levels are proportional to the input probe. If one color (corresponding to a cell type) is selected as the reference color, the ratio-based method can be applied directly. For example, the color red could be selected as the reference, and the intensity level for each of the other probes' colors could be divided by the reference intensity level for red to compute the ratio.

The signals need not correspond to color values. In general, the signals captured from the micro-array represent the quantity of gene expression at particular sites. This quantity can be conveyed via other signal types corresponding to some attribute of the tag or label such as a gray scale intensity, a color intensity, radiation level, etc.

In addition, there are a variety of alternative labeling methods to measure expression levels. The mRNA labeling can be achieved using radiation (P33, P32, etc.), fluorescence (Cy3, Cy5, etc.), chemifluorescence (e.g., alkaline phosphate-based chemifluorescence), physical labels (e.g., biotin labels), or any other direct or indirect labeling as long as signal levels representing the expression levels of each probe can be detected separately. One example of an imaging system suitable for capturing signals representing expression levels is the STORM® image system from Molecular Dynamics, Inc., of Sunnyvale, Calif. This system combines PhosphorImager® system technology with non-radioactive labeling techniques: direct fluorescence and chemifluorescence.

Another aspect of the ratio-based method that may vary depending on the implementation is how and which genes are selected as the internal control genes. Under the null hypothesis, the ratios of every gene expression level possess an identical distribution, regardless of the actual expression levels. However, in practice, not all genes satisfy the null hypothesis. The experiments described above use a set of house-keeping genes, having expression levels that are assumed unchanged in both test samples, for ratio parameter estimation, including the normalization procedure. While this appears to be a preferred approach, it is not necessary to use such a set of control genes in all implementations of the ratio-based method.

There are drawbacks, however, to using a very small sample of genes (e.g., one or two genes selected as a standard with a known ratio) or including every gene in the sample. In the case of a small sample, the entire array will be erroneously calibrated if the standard genes are not correctly detected. In the inclusive approach, every ratio is used without any selection. The result will be biased if a significant fraction of test samples have changed expression levels relative to the reference sample.

A carefully selected internal control gene set with about 100 genes provides a robust calibration result, where the population distribution is estimated even though some of the genes in the pre-selected set may not satisfy the null hypothesis. The confidence interval derived from the distribution can then be applied to the entire array. In other words, the calibration procedure is based on the behavior of a carefully selected set of "housekeeping" genes, as opposed to one or two standard genes or an inclusive set of genes.

The selection of internal control genes can be categorized into three methods: (a) selection by biological house-keeping function, (b) selection by statistical stability over a large collection of array data, and (c) a combination of (a) and (b).

For more information, please see Yidong Chen, Edward R. Dougherty, Michael L. Bittner, "Ratio-Based Decisions and the Quantitative Analysis of cDNA Microarray Images,"

*Journal of Biomedical Optics*, October, 1997, attached as Appendix A, which is hereby incorporated by reference.

In view of the variety of ways in which the invention can be implemented, it is not limited to the specific implementation described above. Instead, the invention includes all that reasonably falls within the scope and spirit of the following claims.

We claim:

1. A method for analyzing gene expression in a cDNA micro-array image, the method comprising:

identifying target sites in the cDNA micro-array image, wherein the target sites are associated with a set of genes;

computing a maximum-likelihood estimator for a coefficient of variation of expression level ratio samples, where the expression level ratio samples are taken from a collection of expression values for each gene in the set of genes associated with the target sites identified in the micro-array image, the expression level ratio samples indicate a ratio of an expression level for a first cell type to an expression level for a second cell type for a corresponding gene, and the expression levels for the corresponding gene are taken from a target site associated with the corresponding gene in the cDNA micro-array image;

computing a confidence interval for the expression level ratio samples based on the maximum likelihood estimator for a coefficient of variation of expression level ratio samples; and identifying genes corresponding to expression level ratio samples outside the confidence interval.

2. The method of claim 1 further including:

initializing an estimated mean for the expression level ratio samples;

(a) calibrating expression level ratio samples by computing a scaling factor between the expression levels of the first and second cell types and adjusting the expression level ratio samples with the scaling factor to generate adjusted expression level ratio samples;

(b) using the maximum likelihood estimator to compute a coefficient of variation of the adjusted expression level ratio samples; and (c) using the coefficient of variation to compute an estimated mean value of the adjusted expression level ratio samples;

repeating the above computations at least once; and after determining the mean and coefficient of variation of the adjusted expression level ratio samples, using the mean and coefficient of variation to compute the confidence interval.

3. The method of claim 2 further including:

capturing the micro-array image for an array of cDNAs hybridized with a first set of labeled mRNAs extracted from the first cell type and a second set of labeled mRNAs extracted from the second cell type, where intensity values of the first set of labeled mRNAs in the micro-array image represent an expression level of the first cell type, and intensity values of the second set of labeled mRNAs represent an expression level of the second cell type; and computing an expression level ratio for each gene in the set as a ratio of an average of the first intensity values to an average of the second intensity values for pixel locations in the identified target site associated with the gene.

4. The method of claim 1 wherein each gene in the set has two or more expression ratios, and each expression ratio represents a ratio of an expression level for a different cell type to an expression level for a reference cell type.

5. The method of claim 1 wherein the expression levels for each gene are determined from intensity values in a portion of the cDNA micro-array image representing a tagged mRNA hybridized to the target site for the gene in a cDNA micro-array.

6. The method of claim 1 wherein mRNAs of the first and second cell types are labeled using a radioactive labeling technique and the expression levels of the first and second cell types for each gene are measured based on presence of radioactive label.

7. The method of claim 1 wherein mRNAs of the first and second cell types are labeled using physical labels and the expression levels of the first and second cell types for each gene are measured based on the physical labels.

8. The method of claim 1 wherein mRNAs of the first and second cell types are labeled using flourescent or chemiflourescent labels and the expression levels of the first and second cell types for each gene are measured based on the flourescent or chemiflourescent labels.

9. A computer readable medium having software for performing the method of claim 1.

10. A programmatic method for analyzing gene expression of two or more cell types in an array of target gene sites, the method comprising:

programmatically extracting expression levels of at least first and second cell types at the target gene sites from an image of the array;

programmatically determining expression level ratios of the first and second cell types at the target gene sites;

programmatically determining a coefficient of variation from the expression level ratios; and based on the coefficient of variation, determining a confidence interval for identifying target sites with expression level ratios that fall outside the confidence interval.

11. The method of claim 10 including:

calibrating the expression levels for first and second cell types at each target site by modifying a measure of the expression level for each cell type by a constant factor for all target sites.

12. The method of claim 10 further including:

iteratively calibrating the expression levels by estimating a constant gain factor between expression levels of the first and second cell types for each gene and then using the estimated constant gain factor to determine a maximum likelihood estimator of the coefficient of variation.

13. A programmatic method for analyzing gene expression of two or more cell types in an array of target gene sites of housekeeping genes, the method comprising:

programmatically extracting expression levels of at least first and second cell types at the target gene sites from an image of the array;

programmatically determining expression levels of the first and second cell types at the target gene sites;

programmatically determining a distribution of the expression levels and a limit in the distribution that is used to identify target sites with an abnormal expression level; and based on the distribution of the expression levels, identifying target sites with expression levels that fall outside the limit.

14. The method of claim 13 wherein the distribution represents a distribution of ratios of expression levels for first and second cell types measured at the target gene sites.

15. The method of claim 13 wherein the expression levels of cell types are measured from intensity levels of the tagged mRNAs of the cell types at the target sites in a micro-array image, and the limit in the distribution is an adaptive confidence interval that is derived by measuring intensity levels of the tagged cell types and background intensity levels and determining the distribution of the intensity levels of the tagged cell types adjusted with the background intensity levels.

16. The method of claim 13 wherein the expression levels are evaluated at each target site within an area where cell expression is detected at the target site and wherein the distribution of expression levels is computed by weighting expression levels at the target sites based on a size of the detected area.

17. The method of claim 13 wherein the distribution of expression levels is computed by weighting expression levels at the target sites such that expression levels are given less weight when a ratio of an expression level to a background level at a target site is less than a threshold amount.

18. The method of claim 13 wherein the distribution of expression levels is computed by weighting expression levels at the target sites such that expression levels are given less weight when a background level measured at a target site differs from a global background level for the array by a threshold amount.

19. A computer-implemented method for analyzing data comprising a plurality of gene expression level ratio samples collected by analyzing a cDNA micro-array image indicating gene expression of a plurality of genes, wherein the ratio samples are associated with the plurality of genes, the method comprising:
  (a) choosing an initial estimate of a mean of a density of the gene expression level ratio samples;
  (b) calibrating the gene expression level ratio samples by applying a gain factor based on the estimate of the mean of the density of the gene expression level ratio samples;
  (c) estimating a coefficient of variation for the gene expression level ratio samples via a maximum-likelihood estimator and the calibrated gene expression level ratio samples;
  (d) re-estimating the mean via the coefficient of variation for the gene expression level ratio samples;
  (e) repeating (b)–(d) at least once; and
  (f) determining a confidence interval via the coefficient of variation estimated by repeating (b)–(d) at least once to identify outlier genes in the data.

20. The method of claim 19 wherein the estimating a coefficient of variation comprises calculating a polynomial regression.

* * * * *

UNITED STATES PATENT AND TRADEMARK OFFICE
CERTIFICATE OF CORRECTION

PATENT NO. : 6,245,517 B1
DATED : June 12, 2001
INVENTOR(S) : Chen et al.

It is certified that error appears in the above-identified patent and that said Letters Patent is hereby corrected as shown below:

<u>Title page,</u>
References Cited, "Dougheryy" should read -- Dougherty --.

<u>Column 6,</u>
Line 9, "$H_0:\mu_X\text{-}\mu_Y=0$" should read -- $H_0:\mu_X\text{-}\mu_Y=0$ --.
Line 10, "$H_1:\mu_X\text{-}\mu_Y=0$" should read -- $H_1:\mu_X\text{-}\mu_Y=0$ --.

<u>Column 7,</u>
Line 18, "$H_1:\mu_{Rk}\ \mu_{Gk}$" should read -- $H_1 : \mu_{Rk} \neq \mu_{Gk}$ --.

<u>Column 11,</u>
Line 11, "$(t'_1, t'_2, \ldots t)$" should read -- $(t'_1, t'_2, \ldots t_n)$ --.
Line 27, "ratio mean p" should read -- ratio mean $\mu$ --.

<u>Column 12,</u>
Line 29, "(see Appendix C." should read -- (see Appendix C). --.

<u>Column 13,</u>
Line 67, "$c_{Rk}$" should read -- $c'_{Rk}$ --.

<u>Column 14,</u>
Line 2, "$\sigma_{BRk} / \sigma_{SRk}$" should read -- $\sigma_{BRk} / \mu_{SRk}$ --.
Line 5, "$c_{Rk} \approx c$" should read -- $c'_{Rk} \approx c$ --.
Line 6, "$c_{Gk}$" should read -- $c'_{Gk}$ --.
Line 51, "$\mu_{BR}$" should read -- $\sigma_{BR}$ --.

The following should appear as Appendix B:

-- Use of a cDNA Microarray to Analyze Gene Expression Patterns in Human Cancer
J. DeRisi [*,+], L. Penland, and P.O. Brown
*Department of Biochemistry, Stanford University Medical Center, Stanford, CA 94305*
M.L. Bittner [*,+], P.S. Meltzer, M. Ray, Y. Chen, Y.A. Su, and J.M. Trent
*Laboratory of Cancer Genetics, National Center for Human Genome Research,
National Institutes of Health, Bethesda, MD 20892*
[*] These two authors contributed equally to this work and their order should be considered arbitrary.
[+] The Stanford/HHMI and NCHGR groups contributed equally to this work.
[Entrez ]
Abstract: The development and progression of cancer and the experimental reversal of tumorigenicity are accompanied by complex changes in patterns of gene expression. cDNA microarrays provide a powerful tool for studying these complex phenomena. Previously we reported that the tumorigenic properties of a human melanoma cell line UACC-903 can be suppressed by introduction of a normal human chromosome 6 [including reduction of growth rate, restoration of contact inhibition, and suppression of both soft agar clonogenicity and tumorigenicity in nude mice]. A high density microarray of 1,161 DNA sequences was used to search for differences in gene expression associated with tumor suppression in this system. Fluorescent probes for hybridization were derived from two sources of cellular mRNA [UACC-903 and UACC-903(+6)] which were labeled with different fluors to provide a direct and internally-controlled comparison of the mRNA levels corresponding to each arrayed gene. The fluorescence signals representing hybridization to each arrayed gene were analyzed to determine the relative abundance in the two samples of mRNAs corresponding to each gene. Previously unrecognized alterations in the expression of specific genes has provided leads for further investigation of the genetic basis of the tumorigenic phenotype of these cells.

Use of a cDNA Microarray to Analyze Gene Expression Patterns in Human Cancer
*Nature Genetics* 14, 457-467, 1996
*Table of EST descriptors and the ratio of red-to-green fluorescence for 88 genes whose function suggests that they may be expressed at relatively constant levels in any cell type.*

| Accession # | Best Match | Red/Green Ratio |
|---|---|---|
| R39171 | Homo sapiens 9G8 splicing factor mRNA, complete cds | 1.411 |
| R38682 | H.sapiens mRNA for splicing factor SF3a120 | 1.217 |
| R13617 | Human transcription elongation factor (SII) mRNA, complete cds | 1.044 |
| R18344 | Human ribosomal protein L5 mRNA, complete cds | 1.376 |
| R18962 | H.sapiens mRNA for elongation factor-1-gamma | 1.161 |
| R45183 | H.sapiens mRNA for elongations factor Tu-mitochondrial | 1.008 |
| R25535 | Human U1 snRNP-specific protein A gene | 1.216 |
| R51346 | Human eIF-2-associated p67 homolog mRNA, complete cds | 1.101 |
| R51355 | Human transcription factor (E2A) mRNA, complete cds | 0.955 |
| R54818 | Human eukaryotic initiation factor 2B-epsilon mRNA, partial cds | 1.038 |
| R54097 | Human translational initiation factor 2 beta subunit (eIF-2-beta) | 1.210 |
| H05919 | Human mRNA for eukaryotic initiation factor 4AII | 1.282 |
| H06853 | Human snRNP polypeptide B mRNA, complete cds | 1.059 |

| H08837 | Human pre-mRNA splicing factor SRp75 mRNA, complete cds | 2.332 |
|---|---|---|
| H09589 | Human mRNA for eukaryotic initiation factor 4AI | 1.059 |
| R16038 | Human transcription factor (TFIIB) mRNA, complete cds | 0.953 |
| R56717 | Human chromatin assembly factor-I p60 subunit mRNA, complete cds | 1.006 |
| R60159 | Human topoisomerase I mRNA, complete cds | 1.108 |
| H17646 | H.sapiens EF-1delta gene encoding human elongation factor-1-delta | 1.543 |
| H21050 | H.sapiens TOP2 mRNA for DNA topoisomerase II (partial) | 1.451 |
| T65293 | Human ADP-ribosylation factor (ARF3) mRNA, complete cds | 1.257 |
| T72604 | Human cytochrome c-1 gene, complete cds | 1.130 |
| T74224 | Human cytochrome b561 gene | 1.418 |
| R12290 | Human cytochrome bc-1 complex core protein II mRNA, complete cds | 1.095 |
| R11842 | Human squalene synthetase (ERG9) mRNA, complete cds | 1.082 |
| R20554 | Human mRNA for phospholipase C-alpha, complete cds | 1.059 |
| R14165 | Homo sapiens phosphatidylinositol 4-kinase mRNA, complete cds | 1.097 |
| R14216 | Human AMP deaminase (AMPD2) mRNA | 1.153 |
| R14305 | Human alpha-N-acetylgalactosaminidase mRNA, complete cds | 1.236 |
| R20115 | H.sapiens G6PD gene for glucose-6-phosphate dehydrogenase | 1.883 |
| R18966 | Human cytosolic aspartate aminotransferase mRNA, complete cds | 1.296 |
| R44005 | Human glutamate decarboxylase (GAD-2) mRNA, complete cds | 1.533 |
| R46044 | Human ALAS1 (ALASH) mRNA for delta-aminolevulinate synthase (housekeeping) (EC 2.3.1.37) | 0.856 |
| R49750 | Human serine dehydratase mRNA, complete cds | 0.843 |
| R51864 | Homo sapiens phosphoglycerate mutase (PGAM-B) mRNA, complete cds | 1.018 |

| | | |
|---|---|---|
| R54023 | Human hydroxymethylglutaryl-CoA lyase mRNA, complete cds | 1.081 |
| R52542 | Human IMP dehydrogenase type 1 mRNA complete cds | 1.093 |
| R59879 | Homo sapiens deoxycytidylate deaminase gene, complete cds | 1.607 |
| R59926 | Human mRNA for cytochrome c oxidase subunit VIc | 1.073 |
| H06630 | Human cytochrome c mRNA, carboxyl-terminal region and 3' non-coding region | 0.844 |
| H09248 | Human aldolase A mRNA, complete cds | 0.935 |
| H28722 | Human ornithine decarboxylase antizyme (Oaz) mRNA, complete cds | 1.527 |
| H28988 | Human mRNA for cytochrome c oxidase subunit IV (EC 1.9.3.1) | 0.931 |
| H17786 | Human phosphoglycerate kinase (pgk) gene | 0.805 |
| H16957 | Human glyceraldehyde 3-phosphate dehydrogenase mRNA | 1.065 |
| H17096 | H.sapiens PMI1 mRNA for phosphomannose isomerase | 1.286 |
| H20545 | Human hexokinase 1 (HK1) mRNA, complete cds | 0.866 |
| R15814 | Human malate dehydrogenase (MDHA) mRNA, complete cds | 1.173 |
| H05914 | Human mRNA for lactate dehydrogenase-A (LDH-A, EC 1.1.1.27) | 1.010 |
| R15151 | Human mRNA for proteasome subunit p31 | 0.801 |
| R18260 | H.sapiens mRNA for seryl-tRNA synthetase | 1.795 |
| R18378 | Human acidic ribosomal phosphoprotein P0 mRNA, complete cds | 1.049 |
| R20424 | Human mRNA for ribosomal protein L32 | 1.553 |
| R20327 | Human 90 kD heat shock protein gene, complete cds | 1.074 |
| R21397 | Human ribosomal protein L29 (humrpl29) mRNA, complete cds | 1.713 |
| R60357 | Human mRNA for alanyl tRNA synthetase | 1.615 |
| H05605 | H.sapiens mRNA for glutaminyl-tRNA synthetase | 0.840 |
| H05893 | Human mRNA for 26S proteasome subunit p97 | 1.147 |
| H05116 | Human mRNA for isoleucyl tRNA synthetase | 0.937 |
| H05285 | H.sapiens QRSHs mRNA for glutaminyl-tRNA synthetase | 1.418 |
| H05820 | Human MRL3 mRNA for ribosomal protein L3 homologue (MRL3=mammalian ribosome L3) | 1.265 |
| H06378 | Human heat shock protein (hsp 70) gene, complete cds | 1.967 |
| H05831 | Human mRNA (KIAA0070) for ORF (related to lysyl tRNA synthetase), partial cds | 0.903 |
| H06711 | Human mRNA for proteasome subunit X | 0.810 |
| H07880 | Human chaperonin protein (Tcp20) gene complete cds | 1.002 |
| H17383 | H.sapiens mRNA for ribosomal protein L3 | 1.590 |
| H19424 | Human ribosomal protein L7a (surf 3) large subunit mRNA, complete cds | 1.974 |
| H23509 | Human mRNA for proteasome subunit HC2 | 0.914 |

| R12732 | Human mRNA for 90-kDa heat-shock protein | 1.409 |
|---|---|---|
| R60149 | Human mRNA for histidyl-tRNA synthetase (HRS) | 1.069 |
| R42924 | Human Na,K-ATPase beta subunit (ATP1B) gene | 0.854 |
| R20438 | Human mRNA for mitochondrial short-chain enoyl-CoA hydratase, complet | 1.143 |
| R24826 | Human mRNA for ATP synthase gamma-subunit (H-type), complete cds | 0.730 |
| R34388 | Human mRNA for mitochobdrial enoyl-CoA hydratase/3-hydroxyacyl-CoA dehydrogenese | 1.104 |
| R53337 | Human mitochondrial ADP/ADT translocator mRNA, complete cds | 1.035 |
| R52962 | Human mRNA for flavoprotein subunit of complex II, complete cds | 1.051 |
| H07926 | Human mRNA for mitochondrial 3-oxoacyl-CoA thiolase, complete cds | 1.516 |
| H11984 | Human Na,K-ATPase alpha-subunit mRNA, complete cds | 0.453 |
| H29169 | H.sapiens mRNA for H+-ATP synthase subunit b | 0.740 |
| H28951 | Human ADP-ribosylation factor mRNA, complete cds | 1.149 |
| H23074 | Human mRNA for mitochondrial 3-ketoacyl-CoA thiolase beta-subunit of trifunctional protein, complete cds | 1.150 |
| R23540 | Human cytoplasmic beta-actin gene, complete cds | 1.038 |
| R26482 | Human mRNA fragment encoding beta-tubulin. (from clone D-beta-1) | 1.245 |
| R53259 | Human gamma-actin mRNA, partial cds | 0.841 |
| R55812 | Human histone (H2A.Z) mRNA, complete cds | 0.610 |
| R59199 | H.sapiens mRNA for beta tubulin, clone nuk 278 | 1.315 |
| H06295 | Human histone H2B.1 mRNA, 3' end | 1.130 |
| H11622 | human alpha-tubulin (from fetal brain) mrna | 1.040 |

--

The following should appear as Appendix C:

--Use of a cDNA Microarray to Analyze Gene Expression Patterns in Human Cancer
*Nature Genetics* 14, 457-467, 1996
*Table of EST descriptors and the ratio of red-to-green fluorescence for all of the named genes designated in the UniGene collection which are found in the Soares normalized infant brain cDNA library.*

| Accession # | Best Match | Red/Green Ratio |
|---|---|---|
| T65376 | Human nucleotide binding protein mRNA, complete cds | 2.549 |
| T65013 | Human protein tyrosine phosphatase (PTPase-alpha) mRNA | 0 |

| | | |
|---|---|---|
| T65005 | Human heparan N-deacetylase/N-sulfotransferase-2 mRNA, complete cds | 0 |
| T65391 | Human helix-loop-helix basic phosphoprotein (G0S8) gene, complete cds | 0 |
| T65118 | Human mRNA for alpha-catenin, complete cds | 1.04 |
| T65121 | Human TFIID subunit TAFII55 (TAFII55) mRNA, complete cds | 1.318 |
| T65293 | Human ADP-ribosylation factor (ARF3) mRNA, complete cds | 1.257 |
| T65070 | Human poly(ADP-ribose) synthetase mRNA, complete cds | 0.531 |
| T64798 | Human Gx-alpha gene | 4.627 |
| T64837 | Human type IV collagenase mRNA, complete cds | 1.016 |
| T65317 | Human pro-alpha-1 (V) collagen mRNA, complete cds | 1.955 |
| T72604 | Human cytochrome c-1 gene, complete cds | 1.13 |
| T74055 | Human mRNA for erythrocyte band 7 integral membrane protein | 0.613 |
| T74119 | Human uroporphyrinogen III synthase mRNA, complete cds | 1.093 |
| T73992 | Human lymphocytic antigen CD59/MEM43 mRNA, complete cds | 0.635 |
| T74224 | Human cytochrome b561 gene | 1.418 |
| T74074 | H.sapiens mRNA for ribosomal protein L26 | 1.011 |
| T74229 | Human hepsin mRNA, complete cds | 1.148 |
| T74308 | H.sapiens ERK3 mRNA | 0.943 |
| T74012 | Human mRNA (KIAA0085) for ORF (novel protein), partial cds | 0.901 |
| T74012 | Human retinoic acid-inducible E3 protein mRNA, complete cds | 1.268 |
| T74095 | Human mRNA for GARS protein, complete cds | 1.056 |
| R39171 | Homo sapiens 9G8 splicing factor mRNA, complete cds | 1.411 |
| R38636 | Human urokinase-type plasminogen activator receptor mRNA, complete cds | 1.249 |
| R43577 | Human extracellular signal-regulated kinase 2 mRNA, complete cds | 0.764 |
| R43581 | Human guanine nucleotide-binding protein G-s, alpha subunit mRNA, partial cds | 1.138 |
| R38539 | Human basic fibroblast growth factor (bFGF) 22.5 kd, 21 kd and 18 kd protein mRNA, complete cds | 0.962 |
| R38682 | H.sapiens mRNA for splicing factor SF3a120 | 1.217 |
| R39239 | Homo sapiens hexabrachion mRNA, complete cds | 0.574 |
| R38668 | Homo sapiens (clone zap128) mRNA, 3' end of cds | 1.1 |
| R38695 | Human SPARC/osteonectin mRNA, complete cds | 1.016 |
| R39522 | Human murine sarcoma 3611 viral (v-raf) oncogene homolog 1 (ARAF1) gene, exons 1-16 | 1.148 |
| R39558 | Human peptidylglycine alpha-amidating monooxygenase mRNA, complete cds | 0.866 |
| R38383 | Human tristetraproline (TTP) mRNA, complete cds | 1.053 |

| R39463 | Human aldolase C gene | 1.499 |
|---|---|---|
| R38178 | Human (clone PSK-J3) cyclin-dependent protein kinase mRNA, complete cds | 0.858 |
| R37855 | Human tumor necrosis factor receptor mRNA, complete cds | 1.057 |
| R37953 | Homo sapiens adenylyl cyclase-associated protein (CAP) mRNA, complete cds | 1.276 |
| R39309 | Human cAMP-dependent protein kinase regulatory subunit type I; complete cds | 0.938 |
| R39334 | Human HLA-B-associated transcript 3 (BAT3) gene, 5' end | 1.159 |
| R38824 | Human gamma-globin mRNA, 3' end | 1.249 |
| R38914 | H.sapiens mRNA for 2.19 gene | 0.931 |
| R37586 | Human ras-related protein (Krev-1) mRNA, complete cds | 1.338 |
| R38717 | Human phosphodiesterase I alpha mRNA | 1.7 |
| R38730 | Human CD34 mRNA, complete cds | 1.319 |
| R38996 | Human mRNA for MTG8 protein, complete cds | 0.996 |
| R39016 | Human dystroglycan (DAG1) mRNA, complete cds | 0.759 |
| R37612 | Human damage-specific DNA binding protein p48 subunit (DDB2) mRNA, complete cds | 1.038 |
| R38987 | Human tropomodulin mRNA, complete cds | 1.553 |
| R38933 | Human tissue plasminogen activator (t-PA) gene, complete cds | 1.315 |
| R38949 | Human EB1 mRNA, complete cds | 1.23 |
| R11718 | Human transcription factor (ITF-2) mRNA, 3' end | 3.041 |
| R12177 | Homo sapiens neuroendocrine-specific protein A (NSP) mRNA, complete cds | 1.509 |
| R11694 | Human mRNA for ORF | 1.099 |
| R11888 | Human biotinidase mRNA, complete cds | 1.5 |
| R12290 | Human cytochrome bc-1 complex core protein II mRNA, complete cds | 1.095 |
| R11842 | Human squalene synthetase (ERG9) mRNA, complete cds | 1.082 |
| R12304 | Human angiotensinogen (AGT) gene | 0.892 |
| R12339 | Homo sapiens beta-globin (HBB) gene, with c to t allele, (J00179 bases 61989-63820) | 7.603 |
| R11946 | Human glutathione S-transferase mRNA, complete cds | 1.736 |
| R12326 | Human mRNA for very low density lipoprotein receptor, complete cds | 1.245 |
| R12517 | H.sapiens GSTT1 mRNA | 1.01 |
| R12545 | Human mRNA for second protein of inter-alpha-trypsin inhibitor complex | 1.479 |
| R12544 | H.sapiens MLN62 mRNA | 1.239 |
| R12634 | Homo sapiens 56K autoantigen annexin XI gene mRNA, complete cds | 1.511 |
| R12860 | Human mRNA for platelet-type phosphofructokinase, complete cds | 1.124 |
| R12750 | Human macrophage mannose receptor (MRC1) gene | 1.367 |
| R20554 | Human mRNA for phospholipase C-alpha, complete cds | 1.059 |

| R12732 | Human mRNA for 90-kDa heat-shock protein | 1.409 |
|---|---|---|
| R13617 | Human transcription elongation factor (SII) mRNA, complete cds | 1.044 |
| R13745 | Human mitotic feedback control protein Madp2 homolog mRNA, complete cds | 0.554 |
| R13991 | Human myristoylated alanine-rich C-kinase substrate mRNA, complete cds | 2.386 |
| R14006 | Human ORF mRNA, complete cds | 1.18 |
| R13895 | Human complement C1r mRNA, complete cds | 1.592 |
| R13658 | Human hepatocyte growth factor(HGF) gene | 1.537 |
| R13819 | Human laminin B2 chain mRNA, complete cds | 1.525 |
| R13904 | Human mRNA for LA45 gene | 1.245 |
| R13936 | Homo sapiens (clone 13a) deoxyhypusine synthase mRNA, complete cds | 1.193 |
| R18790 | Human protein phosphatase 2A alpha subunit mRNA, complete cds | 0.863 |
| R18875 | H.sapiens 63 kDa protein kinase related to rat ERK3 | 1.109 |
| R12998 | Human CLN3 mRNA, complete cds | 1.111 |
| R13980 | Human mRNA (KIAA0092) for ORF (smooth muscle myosin-related), complete cds | 1.064 |
| R12906 | Human liver mRNA fragment DNA binding protein UPI homologue (C-terminus) | 1.136 |
| R40212 | Human coatomer protein (HEPCOP) mRNA, complete cds | 1.247 |
| R13007 | Human smooth muscle cell calponin mRNA, complete cds | 2.667 |
| R14073 | Human mRNA (KIAA0091) for ORF (subtilisin-related), complete cds | 1.287 |
| R13020 | H.sapiens hnRNP-E2 mRNA | 1.036 |
| R13048 | Human Xq28 cosmid, creatine transporter (SLC6A8) gene, complete cds, and CDM gene, partial cds | 1.297 |
| R13051 | Human esterase D mRNA, 3'end | 1.682 |
| R13252 | Human mRNA for 3-oxoacyl-CoA peroxisomal thiolase | 1.297 |
| R13059 | H.sapiens mRNA for PM/Scl 100kD nucleolar protein | 1.092 |
| R40718 | Homo sapiens neuron-specific protein gene, last exon, clone D4S234 | 0.745 |
| R13400 | Human Rch1 (RCH1) mRNA, complete cds | 0.585 |
| R40857 | H.sapiens PR264 gene | 0.958 |
| R14165 | Homo sapiens phosphatidylinositol 4-kinase mRNA, complete cds | 1.097 |
| R14216 | Human AMP deaminase (AMPD2) mRNA | 1.153 |
| R13387 | Human P-glycoprotein (MDR1) mRNA, complete cds | 0 |
| R14197 | Human leukotriene A-4 hydrolase mRNA, complete cds | 1.047 |
| R14296 | Human mRNA (KIAA0034) for ORF (rat cathrin heavy chain homologue), complete cds | 0.681 |
| R14305 | Human alpha-N-acetylgalactosaminidase mRNA, complete cds | 1.236 |

| | | |
|---|---|---|
| R14422 | H.sapiens mRNA for alpha-centractin | 1.217 |
| R14516 | Human GPI-H mRNA, complete cds | 0 |
| R11736 | Human mRNA for senescence marker protein-30 | 0.933 |
| R14593 | Human APX gene encoding APEX nuclease, complete cds | 1.413 |
| R12884 | Human DNA-repair protein (XRCC1) mRNA, complete cds | 1.779 |
| R15123 | Human DNA ligase I mRNA, complete cds | 0 |
| R15125 | Human nuclear autoantigen GS2NA mRNA, complete cds | 2.13 |
| R15151 | Human mRNA for proteasome subunit p31 | 0.801 |
| R15386 | Human ubiquitin carboxyl-terminal hydrolase (PGP 9.5, UCH-L3) isozyme | 2.809 |
| R14924 | H.sapiens mRNA for high endothelial venule | 2.656 |
| R18479 | Human mRNA for liver-type alkaline phosphatase (EC 3.1.3.1) | 9.728 |
| R14692 | Human Na/H antiporter (APNH1) mRNA, complete cds | 1.119 |
| R42244 | H.sapiens RING4 cDNA | 1.292 |
| R18238 | Homo sapiens galactocerebrosidase (GALC) gene | 1.722 |
| R18242 | Human ornithine aminotransferase mRNA, complete cds | 0.686 |
| R18515 | Human MPR46 gene for 46kd mannose 6-phosphate receptor | 0.752 |
| R18518 | Human transformation-sensitive protein (IEF SSP 3521) mRNA, complete | 0 |
| R18151 | Human alternatively spliced trp-1 protein and unspliced trp-1 protein | 1.937 |
| R18638 | Human secretogranin II gene, complete cds | 2.563 |
| R18215 | Human lysosomal glycosylasparaginase (AGA) gene | 1.25 |
| R18344 | Human ribosomal protein L5 mRNA, complete cds | 1.376 |
| R18156 | Human argininosuccinate synthetase gene | 2.545 |
| R18260 | H.sapiens mRNA for seryl-tRNA synthetase | 1.795 |
| R17374 | H.sapiens XAP-4 mRNA for GDP-dissociation inhibitor | 1.335 |
| R17711 | Human mRNA for ORF | 1.149 |
| R17524 | Human mRNA for human homologue of rat phosphatidylethanolamine bindin | 0.942 |
| R17522 | Human decorin (DCN) gene | 14.436 |
| R17537 | Human liver glucokinase (ATP:D-hexose 6-phosphotransferase) mRNA, com | 0.944 |
| R17511 | Human 80K-H protein (kinase C substrate) mRNA, complete cds | 1.341 |
| R17793 | Human mismatch repair (hMLH1) gene | 0 |
| R18363 | H.sapiens hTGR 1 mRNA | 0 |
| R18378 | Human acidic ribosomal phosphoprotein P0 mRNA, complete cds | 1.049 |
| R17500 | H.sapiens MLN64 mRNA | 1.657 |
| R17499 | Human MAL protein gene mRNA, complete cds | 1.488 |
| R17515 | Human capping protein alpha mRNA, partial cds | 1.177 |
| R18437 | Human epoxide hydrolase mRNA, complete cds | 1.086 |

| R17785 | Human mercurial-insensitive water channel mRNA, form 2, complete cds | 1.174 |
|---|---|---|
| R21451 | Homo sapiens brain thiol-specific antioxidant protein mRNA, complete | 0.863 |
| R20852 | Human mRNA for protein phosphatase 2A (beta-type) | 0.947 |
| R42854 | H.sapiens Id1 mRNA | 2.239 |
| R20866 | Human ubiquitin gene (3 repeats) | 1.891 |
| R20868 | Human mRNA (KIAA0088) for ORF (alpha-glucosidase-related), partial cd | 1.802 |
| R17143 | Human platelet-derived growth factor (PDGF) receptor mRNA, complete c | 0 |
| R17312 | H.sapiens mRNA for novel DNA binding protein | 0.807 |
| R17250 | Human male-enhanced antigen mRNA (Mea), complete cds | 2.204 |
| R17253 | Human syntaxin 5 mRNA, complete cds | 0 |
| R17846 | Human protein phosphatase I alpha subunit (PPPIA) mRNA, 3' end | 1.832 |
| R17610 | Human farnesyltransferase alpha-subunit mRNA, complete cds | 0 |
| R42891 | Human mRNA for ORF, Xq terminal portion | 1.038 |
| R17555 | Human Ca2+-dependent activator protein for secretion mRNA, complete c | 0 |
| R17444 | Human mRNA for protein gene product (PGP) 9.5 | 0.98 |
| R42897 | Human mRNA (HA1756) for ORF, complete cds | 0 |
| R17345 | Human phosphorylase kinase (PSK-C3) mRNA, complete cds | 0 |
| R42924 | Human Na,K-ATPase beta subunit (ATP1B) gene | 0.854 |
| R17453 | H.sapiens hPTPA mRNA | 1.428 |
| R43287 | Human platelet alpha SNAP mRNA, complete cds | 2.064 |
| R43734 | H.sapiens mRNA for laminin alpha4 | 1.518 |
| R18736 | H.sapiens NAP (nucleosome assembly protein) mRNA, complete cds | 1.888 |
| R18761 | Human B cell differentiation antigen mRNA, complete cds | 1.178 |
| R18918 | Human MAR/SAR DNA binding protein (SATB1) mRNA, complete cds | 1.214 |
| R20216 | H.sapiens mRNA for vacuolar proton ATPase, subunit E | 1.049 |
| R20115 | H.sapiens G6PD gene for glucose-6-phosphate dehydrogenase | 1.883 |
| R43196 | Human apolipoprotein J mRNA, complete cds | 2.63 |
| R20422 | H.sapiens vimentin gene | 0.938 |
| R20424 | Human mRNA for ribosomal protein L32 | 1.553 |
| R20354 | Homo sapiens Huntington's Disease (HD) gene and mRNA, complete cds | 1.101 |
| R43628 | H.sapiens sds22-like mRNA | 1.193 |
| R20118 | H.sapiens serum paraoxonase (PON) mRNA, complete cds | 0.877 |
| R43520 | Homo sapiens homolog of mouse MAT-1 oncogene mRNA, complete cds | 1.379 |
| R20430 | Human (hMSH2) mRNA, complete cds | 1.603 |

| R20357 | Human Gps1 (GPS1) mRNA, complete cds | 1.263 |
|---|---|---|
| R20232 | Human ionizing radiation resistance conferring protein mRNA, complete | 1.2 |
| R20438 | Human mRNA for mitochondrial short-chain enoyl-CoA hydratase, complet | 1.143 |
| R19322 | Human aldose reductase mRNA, complete cds | 3.763 |
| R19478 | Human neuropeptide Y peptide YY receptor mRNA, complete cds | 1.236 |
| R18936 | Human mRNA for ribophorin II | 0.839 |
| R18814 | Human mRNA for cathepsin H (E.C.3.4.22.16.) | 0.754 |
| R19505 | Human insulin-like growth factor binding protein 2 (IGFBP2) mRNA, com | 0.831 |
| R19508 | Human mRNA | 0.853 |
| R18956 | Human DNA for plasma glutathione peroxidase, exon 3, 4 and 5 | 1.309 |
| R19071 | Homo sapiens (TAFII70-alpha) mRNA, complete cds | 1.512 |
| R18978 | H.sapiens mRNA for phenylalkylamine binding protein | 1.391 |
| R18962 | H.sapiens mRNA for elongation factor-1-gamma | 1.161 |
| R43903 | Human mRNA (KIAA0100) for ORF (human counterpart of mouse e1 gene), c | 1.261 |
| R18966 | Human cytosolic aspartate aminotransferase mRNA, complete cds | 1.296 |
| R44005 | Human glutamate decarboxylase (GAD-2) mRNA, complete cds | 1.533 |
| R18985 | H.sapiens HPBRII-4 mRNA | 1.151 |
| R18986 | Human aldehyde dehydrogenase 2 mRNA | 0.777 |
| R24826 | Human mRNA for ATP synthase gamma-subunit (H-type), complete cds | 0.73 |
| R24851 | Homo sapiens (clone S240ii117/zap112) mRNA, complete cds | 0.793 |
| R19940 | Human RNA helicase A mRNA, complete cds | 0 |
| R19843 | Human beta-galactosidase (GLB1) mRNA, complete cds | 0.906 |
| R19842 | Homo sapiens tyrosine phosphatase (IA-2/PTP) mRNA, complete cds | 1.053 |
| R23516 | Human mRNA for T-cell cyclophilin | 1.058 |
| R24838 | Human clone pSK1 interferon gamma receptor accessory factor-1 (AF-1) | 0 |
| R19835 | Human HLA-B-associated transcript 2 (BAT2) gene, 5' flank | 1.088 |
| R20157 | Human mRNA for glucocerebrosidase, complete cds | 2.625 |
| R23392 | Human p58 protein kinase (clk-1) gene | 3.09 |
| R23416 | Homo sapiens catechol-O-methyltransferase (COMT) mRNA, complete cds | 1.284 |
| R24993 | H.sapiens mRNA for transcription factor TFIIE beta | 0 |
| R20444 | Human cellular oncogene c-fos (complete sequence) | 1.535 |
| R23540 | Human cytoplasmic beta-actin gene, complete cds | 1.038 |

| | | |
|---|---|---|
| R23395 | Human non-histone chromosomal protein HMG-14 mRNA, complete cds | 1.769 |
| R23538 | Human mRNA for calmodulin | 1.141 |
| R20327 | Human 90 kD heat shock protein gene, complete cds | 1.074 |
| R20178 | Human liver mRNA for beta-subunit signal transducing proteins Gs/Gi ( | 1.078 |
| R20464 | Human mRNA for La protein C-terminal region | 1.627 |
| R19727 | Human HLA-E class I mRNA | 2.396 |
| R25016 | Homo sapiens T cell activation antigen (CD27) mRNA, complete cds | 1.595 |
| R19621 | Human mRNA for Nm23 protein, involved in developmental regulation (ho | 0.863 |
| R19814 | Homo sapiens signal recognition particle subunit 9 (SRP9) mRNA, compl | 0.89 |
| R19650 | H.sapiens mRNA for ragA protein | 1 |
| R45054 | Human gene encoding prepro form of corticotropin releasing factor | 1.35 |
| R19653 | Human mRNA (KIAA0026) for ORF (complete cds) and HepG2 mRNA identical | 1.842 |
| R19634 | Human mRNA for basigin | 1.838 |
| R45183 | H.sapiens mRNA for elongations factor Tu-mitochondrial | 1.008 |
| R19668 | Homo sapiens(clone 71) Miller-Dieker lissencephaly protein (LIS1) mRN | 1.325 |
| R25078 | Human GM2-activator protein (GM2A) mRNA, complete cds | 1.264 |
| R24950 | H.sapiens mRNA for protein phosphatase 5 | 1.348 |
| R24981 | Human protein phosphatase 2A beta subunit mRNA, complete cds | 0 |
| R45405 | Human mRNA for F1-ATPase beta subunit (F-1 beta) | 0.668 |
| R25091 | Human guanine nucleotide regulatory protein (nep1) mRNA, complete cds | 1.633 |
| R25535 | Human U1 snRNP-specific protein A gene | 1.216 |
| R21274 | H.sapiens mitoxantrone-resistance associated mRNA | 1.159 |
| R14985 | Human chromosome 17q12-21 mRNA, clone pOV-3, partial cds | 1.538 |
| R15001 | Human mRNA for DNA-binding protein TAXREB302, complete cds | 1.758 |
| R14648 | Human muscle glycogen synthase mRNA | 1.651 |
| R46044 | Human ALAS1 (ALASH) mRNA for delta-aminolevulinate synthase (housekeeping) (EC 2.3.1.37) | 0.856 |
| R20685 | Human ENO2 gene for neuron specific (gamma) enolase | 1.74 |
| R22837 | Human calphobindin II mRNA, complete cds | 2.179 |
| R20594 | Human glutathione transferase class mu number 4 (GSTM4) mRNA, complete cds | 1.517 |
| R21050 | Human zinc finger protein ZNF133 | 2.779 |

| | | |
|---|---|---|
| R21329 | Homo sapiens (clone 1950.2) interferon-gamma IEF SSP 5111 mRNA, complete cds | 2.592 |
| R21055 | Human mRNA (HA1523) for ORF, partial sequence | 1.615 |
| R21374 | Human mRNA for fibronectin (FN precursor) | 5.6 |
| R21397 | Human ribosomal protein L29 (humrpl29) mRNA, complete cds | 1.713 |
| R21092 | Human cDNA for carbonic anhydrase I | 0 |
| R46584 | H. sapiens mRNA for protein phosphatase X | 1.328 |
| R25823 | Human t-complex polypeptide 1 gene | 1.484 |
| R25270 | Human amyloid protein (AD-AP) mRNA, 3' end | 1.137 |
| R25807 | Human DNF1552 (lung) mRNA, complete cds | 1.121 |
| R25713 | H.sapiens BBC1 mRNA | 1.454 |
| R25309 | H.sapiens mRNA for IgM heavy chain constant region (mAb61) | 4.11 |
| R25816 | H.sapiens mRNA for A2b adenosine receptor | 1.601 |
| R25566 | Human B12 protein mRNA, complete cds | 2.254 |
| R34388 | Human mRNA for mitochobdrial enoyl-CoA hydratase/3-hydroxyacyl-CoA dehydrogenese alpha-subunit of trifunctional protein, complete cds | 1.104 |
| R34634 | H.sapiens mRNA for glycogenin | 1.669 |
| R34420 | Human mRNA for polypeptide 7B2 | 0 |
| R34906 | H.sapiens mRNA for interleukin-1 receptor antagonist | 1.13 |
| R34639 | Human mRNA for CIRP | 1.659 |
| R34651 | Homo sapiens MHC HLA-B39 mRNA, complete cds | 1.547 |
| R34544 | Human mRNA for p68 protein | 1.325 |
| R34548 | Human high density lipoprotein binding protein (HBP) mRNA, complete cds | 0 |
| R34912 | Human liver-type 1-phosphofructokinase (PFKL) mRNA, complete cds | 0.989 |
| R35138 | Human alternative guanine nucleotide-binding regulatory protein (G) alpha-inhibitory-subunit mRNA, complete cds | 2.134 |
| R35021 | Human recombinant glial growth factor 2 mRNA, complete cds and flanking regions | 1.648 |
| R49278 | Human lysyl oxidase-like protein gene | 1.393 |
| R34646 | Human mRNA for motor protein, complete cds | 0.869 |
| R49285 | Human mRNA for inport precursor of human ATP synthase alpha subunit | 1.665 |
| R35145 | Human Xq28 cosmid, creatine transporter (SLC6A8) gene, complete cds, and CDM gene, partial cds | 1.26 |
| R35151 | Human protective protein mRNA, complete cds | 1.506 |
| R35152 | Homo sapiens connexin 37 (GJA4) mRNA, complete cds | 1.443 |
| R35283 | Human B lymphocyte serine/threonine protein kinase mRNA, complete cds | 2.068 |
| R26502 | Human prolidase (imidodipeptidase) mRNA, complete cds | 1.346 |
| R35185 | Human Ia-associated invariant gamma-chain gene | 1.126 |

| R26482 | Human mRNA fragment encoding beta-tubulin. (from clone D-beta-1) | 1.245 |
|---|---|---|
| R26508 | Human proalpha 1 (I) chain of type I procollagen mRNA (partial) | 1.288 |
| R35277 | Human carbonyl reductase mRNA, complete cds | 0 |
| R35276 | H.sapiens OXA1Hs mRNA | 1.763 |
| R35294 | Homo sapiens creatine kinase B mRNA, complete cds | 1.219 |
| R26627 | Human c-myc binding protein (MBP-1) mRNA, complete cds | 1.107 |
| R26511 | Human mRNA for carboxypeptidase E (EC 3.4.17.10) | 1.474 |
| R35538 | Human 12S RNA induced by poly(rI), poly(rC) and Newcastle disease virus | 1.168 |
| R35542 | Human spinal muscular atrophy gene product mRNA, complete cds | 1.233 |
| R35402 | Human methylmalonyl-CoA mutase (MCM) mRNA, complete cds | 1.826 |
| R61502 | Human tumor necrosis factor type 1 receptor associated protein (TRAP1) mRNA, partial cds | 1.646 |
| R59378 | Human mRNA (KIAA0025) for ORF (complete cds) and PIGHEP3 homologous region | 1.159 |
| R61352 | Human mRNA (KIAA0095) for ORF (yeast NIC96 gene-related), complete cds | 0.738 |
| R59298 | Human DNA for osteopontin, complete cds | 0.155 |
| R59300 | Human ubiquitin mRNA, complete cds | 0.772 |
| R61492 | Human mRNA for rod photoreceptor protein | 1.337 |
| R59307 | Human protein kinase mRNA, complete cds | 1.134 |
| R60589 | H.sapiens mRNA for protein tyrosine phosphatase | 1.659 |
| R60591 | Human (clone N5-4) protein p84 mRNA, complete cds | 1.242 |
| R35433 | H.sapiens mRNA for mitochondrial phosphate carrier protein | 2.121 |
| R49034 | Human connective tissue growth factor, complete cds | 1.414 |
| R35961 | H.sapiens mRNA for cyclin H assembly factor | 1.152 |
| R36315 | Human mRNA for protein-tyrosine-phosphatase G1, complete cds | 1.494 |
| R51491 | Human mRNA for plasma gelsolin | 1.055 |
| R51310 | Human lipoprotein lipase mRNA, complete cds | 0 |
| R49711 | Human placental calpastatin mRNA, partial cds | 3.308 |
| R49750 | Human serine dehydratase mRNA, complete cds | 0.843 |
| R36036 | Human 100 kDa coactivator mRNA, complete cds | 0.731 |
| R50771 | Human mRNA for protein-tyrosine phosphatase | 0.549 |
| R50800 | Homo sapiens growth-arrest-specific protein (gas) mRNA, complete cds | 0.844 |
| R51036 | Human thrombospondin 2 (THBS2) mRNA, complete cds | 0.34 |
| R49755 | Homo sapiens (clone hKvBeta3) K+ channel beta subunit mRNA, complete cds | 0.808 |
| R54403 | Human Ca2-activated neutral protease large subunit (CANP) mRNA, complete cds | 3.089 |

| | | |
|---|---|---|
| R52354 | Human placental FXIIIa mRNA, complete cds | 0 |
| R54440 | Human dynamin mRNA, alternative exon and 3' end of cds | 0 |
| R51346 | Human eIF-2-associated p67 homolog mRNA, complete cds | 1.101 |
| R51837 | Human fibromodulin mRNA, partial cds | 1.484 |
| R51864 | Homo sapiens phosphoglycerate mutase (PGAM-B) mRNA, complete cds | 1.018 |
| R54353 | Human 26-kDa cell surface protein TAPA-1 mRNA, complete cds | 1.258 |
| R54411 | H.sapiens mRNA for a cell surface protein | 1.071 |
| R52366 | H.sapiens mRNA for BCL7B protein | 0 |
| R51355 | Human transcription factor (E2A) mRNA, complete cds | 0.955 |
| R51875 | Human bcr mRNA (break point cluster gene) | 0.566 |
| R54424 | Human liver glutamate dehydrogenase mRNA, complete cds | 1.188 |
| R51899 | Human somatostatin I gene and flanks | 1.536 |
| R54457 | Human insulin-like growth factor (IGF) binding protein mRNA, complete cds | 0.69 |
| R52489 | Human mRNA (KIAA0028) for ORF, complete cds | 0.683 |
| R51897 | Homo sapiens (lambda-gt11ht-5) MHC class I antigen-like glycoprotein (CD1D) mRNA, complete cds | 0.981 |
| R52403 | Human mRNA for ORF, complete cds | 1.593 |
| R54579 | Human melanoma-associated antigen ME491 mRNA, complete cds | 0.783 |
| R54023 | Human hydroxymethylglutaryl-CoA lyase mRNA, complete cds | 1.081 |
| R53355 | Human 136-kDa double-stranded RNA binding protein p136 (K88dsRBP) mRNA, complete cds | 0.659 |
| R51999 | Human placental ribonuclease inhibitor mRNA, complete cds | 0.198 |
| R54563 | H.sapiens mRNA for acetylcholine receptor (epsilon subunit) | 0.97 |
| R52542 | Human IMP dehydrogenase type 1 mRNA complete cds | 1.093 |
| R54027 | Human (HepG2) glucose transporter gene mRNA, complete cds | 4.657 |
| R53563 | Human 22kDa smooth muscle protein (SM22) mRNA, complete cds | 2.147 |
| R52548 | Human superoxide dismutase (SOD-1) mRNA, complete cds | 1.123 |
| R54031 | Human myelin proteolipid protein mRNA, complete cds | 0 |
| R53337 | Human mitochondrial ADP/ADT translocator mRNA, complete cds | 1.035 |
| R54043 | Human zinc finger protein ZNF140 | 1.447 |
| R52637 | Human prealbumin mRNA in individuals with familial amyloidotic polyneuropathy (FAP), complete cds | 1.167 |
| R52638 | Human mRNA for transcription factor AREB6, complete cds | 0.803 |
| R53380 | Human apolipoprotein D mRNA, complete cds | 0.691 |
| R52103 | Human cathepsin B proteinase mRNA, complete cds | 1.082 |
| R55655 | Human HHR6A (yeast RAD 6 homologue) mRNA, complete cds | 1.103 |

| R52962 | Human mRNA for flavoprotein subunit of complex II, complete cds | 1.051 |
|---|---|---|
| R54818 | Human eukaryotic initiation factor 2B-epsilon mRNA, partial cds | 1.038 |
| R53259 | Human gamma-actin mRNA, partial cds | 0.841 |
| R53074 | Homo sapiens adenosine triphosphatase mRNA, complete cds | 0 |
| R53076 | Homo sapiens Hepatitis B virus X-associated protein 1 mRNA, complete cds | 0.771 |
| R55360 | Homo sapiens GT197 partial ORF mRNA, 3' end of cds | 1.371 |
| R54807 | Human beta-sarcoglycan dystrophin-associated glycoprotein mRNA, complete cds | 0 |
| R56041 | H.sapiens a2-chimaerin mRNA | 1.933 |
| R56245 | Human AD amyloid mRNA, complete cds | 0.661 |
| R56246 | human hla-dr antigen alpha-chain mrna & ivs fragments | 1.044 |
| R55760 | Human mitogen induced nuclear orphan receptor (MINOR) mRNA, complete cds | 1.346 |
| R56439 | Human gamma-tubulin mRNA, complete cds | 0.909 |
| R56560 | Homo sapiens dbpB-like protein mRNA, complete cds | 0.778 |
| R55812 | Human histone (H2A.Z) mRNA, complete cds | 0.61 |
| R56229 | Human adenine nucleotide translocator-2 (ANT-2) gene, complete cds | 0.755 |
| R56065 | Human c-jun proto oncogene (JUN), complete cds, clone hCJ-1 | 0.675 |
| R56711 | Human tie mRNA for putative receptor tyrosine kinase | 0 |
| R56773 | Homo sapiens (clone KT2) bone morphogenetic protein-1 (BMP-1) mRNA and alternatively spliced mammalian tolloid protein (mTld) | 0 |
| R56717 | Human chromatin assembly factor-I p60 subunit mRNA, complete cds | 1.006 |
| R59164 | Homo sapiens protein phosphatase 2A B56-alpha mRNA, complete cds | 1.126 |
| R56124 | Human src-like kinase (slk) mRNA, complete cds | 1.068 |
| R58964 | Human cofilin mRNA, partial cds | 1.37 |
| R58991 | Spermidine/spermine N1-acetyltransferase mRNA, complete cds | 0.97 |
| R54097 | Human translational initiation factor 2 beta subunit (elF-2-beta) mRNA, complete cds | 1.21 |
| R52820 | Human ubiquitin-like protein (GdX) gene, complete cds | 0.904 |
| R52875 | H. sapiens cDNA for RFG | 1.176 |
| R59543 | H.sapiens mRNA for nuclear factor RIP140 | 0.755 |
| R59199 | H.sapiens mRNA for beta tubulin, clone nuk 278 | 1.315 |
| R54087 | Human glucose transporter-like protein-III (GLUT3), complete cds | 2.173 |
| R52706 | Human gene for PP15 (placental protein 15) | 2.2 |

| R60247 | Human palmitoylated erythrocyte membrane protein (MPP1) mRNA, complete cds | 1.14 |
|---|---|---|
| R60738 | Human MAC25 mRNA, complete cds | 2.324 |
| R60316 | Homo sapiens epidermal growth factor receptor-binding protein GRB2 (EGFRBP-GRB2) mRNA sequence | 1.014 |
| R60317 | Human dihydrolipoamide dehydrogenase mRNA, complete cds | 0.96 |
| R61686 | Human PMI gene for a putative receptor protein | 1.248 |
| R60933 | Human cytoplasmic chaperonin hTRiC5 mRNA, partial cds | 1.039 |
| R60749 | Homo sapiens thyroid receptor interactor (TRIP6) mRNA, 3' end of cds | 1.12 |
| R59598 | Homo sapiens protein tyrosine kinase (Syk) mRNA, complete cds | 1.187 |
| R60357 | Human mRNA for alanyl tRNA synthetase | 1.615 |
| R60916 | Human prothymosin alpha mRNA, complete cds | 1.102 |
| R59748 | Human 14-3-3 protein mRNA, complete cds | 1.255 |
| R59750 | Human ADP/ATP translocase mRNA, 3' end, clone pHAT8 | 1.048 |
| R59777 | H.sapiens mRNA for NADP+-dependent malic enzyme | 3.108 |
| R59972 | Human mRNA for protein kinase C (PKC) type beta II | 1.817 |
| R61084 | Homo sapiens calcium-ATPase (HK2) mRNA, complete cds | 0.902 |
| R59791 | Human ubiquitin-activating enzyme E1 (UBE1) mRNA, complete cds | 1.234 |
| R60966 | Homo sapiens (huc) mRNA, complete cds | 1.14 |
| R61204 | Homo sapiens transketolase (tk) mRNA, complete cds | 1.389 |
| R59879 | Homo sapiens deoxycytidylate deaminase gene, complete cds | 1.607 |
| R60871 | H.sapiens TUP1-like enhancer of split gene 1 (TUPLE1) mRNA | 1.474 |
| R59695 | Human GST1-Hs mRNA for GTP-binding protein | 0 |
| R60225 | Human peroxisomal targeting signal receptor 1 (PXR1) mRNA, complete cds | 0 |
| R59922 | Human nuclear factor NF45 mRNA, complete cds | 0.672 |
| R59725 | Human IEF SSP 9502 mRNA, complete cds | 1.179 |
| R60019 | H.sapiens mRNA for DLG2 | 0 |
| R60023 | H.sapiens NADP+ dependent cytoplasmic malic enzyme mRNA | 0 |
| R60171 | Human signal-transducing guanine nucleotide-binding regulatory (G) protein beta subunit mRNA, complete cds | 0 |
| R59926 | Human mRNA for cytochrome c oxidase subunit VIc | 1.073 |
| R60149 | Human mRNA for histidyl-tRNA synthetase (HRS) | 1.069 |
| R60527 | H.sapiens mRNA for ch-TOG protein | 0 |
| R59709 | Human MIC2 mRNA, complete cds | 1.03 |
| R59743 | Human tra1 mRNA for human homologue of murine tumor rejection antigen gp96 | 1.346 |

| R60159 | Human topoisomerase I mRNA, complete cds | 1.108 |
|---|---|---|
| H05605 | H.sapiens mRNA for glutaminyl-tRNA synthetase | 0.84 |
| H05891 | Human proliferating cell nuclear antigen (PCNA) gene, complete cds | 0.722 |
| H05893 | Human mRNA for 26S proteasome subunit p97 | 1.147 |
| H05899 | Human nuclear ribonucleoprotein particle (hnRNP) C protein mRNA, complete cds | 1.17 |
| H05919 | Human mRNA for eukaryotic initiation factor 4AII | 1.282 |
| H05613 | Homo sapiens hepatoma transmembrane kinase ligand (HTK ligand) mRNA, complete cds | 1.371 |
| H05603 | Human c-erbA-alpha-2 gene encoding thyroid hormone receptor type alpha-2 mRNA, complete cds, clone hTR-alpha-2 | 0.941 |
| H05639 | Homo sapiens (clone B6a) focal adhesion kinase (FAK2) mRNA, complete cds | 8.248 |
| H05913 | H.sapiens M gene for M1-type and M2-type pyruvate kinase | 1.41 |
| H05914 | Human mRNA for lactate dehydrogenase-A (LDH-A, EC 1.1.1.27) | 1.01 |
| H05935 | Human sterol 27-hydroxylase (CYP27) mRNA, complete cds | 1.075 |
| H05727 | Human butyrylcholinesterase (BChEG1) gene | 0.069 |
| H06193 | Human glutamate receptor 2 (HBGR2) mRNA, complete cds | 1.217 |
| H04787 | Human Ku autoimmune antigen gene, complete cds | 1.478 |
| H05736 | Human steroid 5-alpha-reductase mRNA, complete cds | 1.638 |
| H05761 | Human protein phosphatase 2A-alpha catalytic subunit mRNA, complete cds | 1.351 |
| H05768 | H.sapiens mRNA for subunit C of vacuolar proton-ATPase V1 domain | 1.339 |
| H04823 | H.sapiens mRNA for receptor protein tyrosine kinase | 1.378 |
| H05116 | Human mRNA for isoleucyl tRNA synthetase | 0.937 |
| H04825 | Human RSU-1/RSP-1 mRNA, complete cds | 2.248 |
| H05982 | Human FK506-binding protein (FKBP) mRNA, complete cds | 1.026 |
| H06149 | H.sapiens MLN50 mRNA | 0.98 |
| H05272 | Human mRNA for ORF | 1.188 |
| H06479 | H.sapiens MacMarcks mRNA | 0.587 |
| H06510 | H.sapiens RbAp48 mRNA encoding retinoblastoma binding protein | 0.925 |
| H06516 | Human alpha-2-macroglobulin mRNA, complete cds | 1.19 |
| H06515 | H.sapiens TEGT gene | 2.462 |
| H06272 | Human vinculin mRNA, complete cds | 2.739 |
| H05285 | H.sapiens QRSHs mRNA for glutaminyl-tRNA synthetase | 1.418 |
| H05820 | Human MRL3 mRNA for ribosomal protein L3 homologue ( MRL3=mammalian ribosome L3 ) | 1.265 |
| H06487 | H.sapiens PROS-27 mRNA | 1.23 |
| H06378 | Human heat shock protein (hsp 70) gene, complete cds | 1.967 |
| H06295 | Human histone H2B.1 mRNA, 3' end | 1.13 |

| | | |
|---|---|---|
| H06297 | H.sapiens MGF gene exons 1&2 | 0.452 |
| H05831 | Human mRNA (KIAA0070) for ORF (related to lysyl tRNA synthetase), partial cds | 0.903 |
| H06300 | Homo sapiens iduronate-2-sulfatase (IDS) gene | 0.91 |
| H07071 | Human vascular cell adhesion molecule 1 mRNA, complete cds | 0.982 |
| H06613 | H.sapiens HSJ1 mRNA | 4.243 |
| H06726 | Human mRNA (KIAA0045) for ORF, complete cds | 1.676 |
| H06853 | Human snRNP polypeptide B mRNA, complete cds | 1.059 |
| H05445 | Human neuronal growth protein 43 (GAP-43) mRNA, complete cds | 1.399 |
| H07079 | Human RIG mRNA, complete sequence | 1.372 |
| H06623 | Human RhD blood group antigen mRNA, complete cds | 1.932 |
| H05450 | Human Ku protein subunit mRNA, complete cds | 1.48 |
| H07085 | Human retinoblastoma-binding protein (RbAp46) mRNA, complete cds | 1.134 |
| H06602 | Human proton ATPase homologue mRNA, 3' end | 0.454 |
| H06630 | Human cytochrome c mRNA, carboxyl-terminal region and 3' non-coding region | 0.844 |
| H06711 | Human mRNA for proteasome subunit X | 0.81 |
| H06712 | H.sapiens mRNA for transcript associated with monocyte to macrophage differentiation | 3.302 |
| H08826 | Human non-histone chromosomal protein HMG-17 mRNA, complete cds | 3.645 |
| H05245 | Human mRNA for ezrin | 1.461 |
| H07880 | Human chaperonin protein (Tcp20) gene complete cds | 1.002 |
| H08642 | Human atrophin-1 mRNA, complete cds | 1.114 |
| H07926 | Human mRNA for mitochondrial 3-oxoacyl-CoA thiolase, complete cds | 1.516 |
| H08531 | Human transforming growth factor-beta induced gene product (BIGH3) mRNA, complete cds | 1.496 |
| H05264 | Human zinc-finger protein 7 (ZFP7) mRNA, complete cds | 1.332 |
| H09732 | Human kidney mRNA for catalase | 1.378 |
| H08207 | H.sapiens mRNA for BCL7A protein | 1.002 |
| H08469 | Human N-acetyl-beta-glucosaminidase (HEXB) mRNA, 3' end | 1.652 |
| H05258 | Human mRNA for ORF, complete cds | 1.452 |
| H09309 | Human cDNA for uracil-DNA glycosylase | 0 |
| H08667 | Human collagen type XVIII alpha 1 (COL18A1) mRNA, partial cds | 1.539 |
| H08837 | Human pre-mRNA splicing factor SRp75 mRNA, complete cds | 2.332 |
| H09054 | H.sapiens mRNA for DNA (cytosin-5)-methyltransferase | 1.167 |
| H09351 | Human mRNA for hMCM2, complete cds | 0.853 |
| H09007 | Homo sapiens PP2A B56-beta mRNA, complete cds | 1.52 |
| H09589 | Human mRNA for eukaryotic initiation factor 4AI | 1.059 |

| ID | Description | Value |
|---|---|---|
| H09636 | H.sapiens dek mRNA | 1.031 |
| H09248 | Human aldolase A mRNA, complete cds | 0.935 |
| H09250 | Human mRNA for translationally controlled tumor protein | 1.297 |
| H10642 | Human F-actin capping protein beta subunit mRNA, complete cds | 2.447 |
| H09662 | Human mRNA for raf oncogene | 0 |
| H09931 | Human heparan sulfate N-deacetylase/N-sulfotransferase mRNA, complete cds | 0 |
| H09171 | H.sapiens HRPL4 mRNA | 1.087 |
| H09646 | Human serum albumin (ALB) mRNA | 0 |
| H10674 | Human mRNA (KIAA0056) for ORF, partial cds | 0 |
| H09666 | Human CDC42 GTPase-activating protein mRNA, partial cds | 1.244 |
| H09782 | Human mRNA for G(i) protein alpha-subunit (adenylate cyclase inhibiting GTP-binding protein) | 1.58 |
| H10217 | Human splicing factor SRp30c mRNA, complete cds | 1.359 |
| H09797 | Human scar protein mRNA, complete cds | 1.141 |
| H10227 | H.sapiens mRNA for protein phosphatase 1 gamma | 1.452 |
| H10052 | Human LTG9/MLLT3 mRNA, C-terminal | 1.287 |
| H10960 | Human mRNA for ORF, complete cds | 0 |
| H11069 | Human mRNA for heterogeneous nuclear ribonucleoprotein D (hnRNP D) | 1.163 |
| H10836 | Human mRNA for cathepsin D from oestrogen responsive breast cancer cells | 1.299 |
| H11049 | Human ADP-ribosylation factor 1 (ARF1) mRNA, complete cds | 1.001 |
| H10841 | Human mRNA for GABA-A receptor, alpha 1 subunit | 1.496 |
| H11054 | Human mRNA for protein kinase C delta-type | 0 |
| H10950 | Human mRNA for adrenomedullin, complete cds | 0 |
| H10847 | Human chaperonin (HSP60) mRNA, complete cds | 3.922 |
| H11003 | Homo sapiens endothelin-1 (EDN1) gene, complete cds | 2.3 |
| H10778 | Human methylenetetrahydrofolate dehydrogenase-methenyltetrahydrofolate cyclohydrolase-formyltetrahydrofolate synthetase mRNA, complete cds | 0 |
| H10391 | Human alpha-1-antichymotrypsin mRNA, 3' end | 0.152 |
| H11921 | Human mRNA for ORF | 0 |
| H12043 | Homo sapiens inducible protein mRNA, complete cds | 1.098 |
| H11583 | Human Nip1 (NIP1) mRNA, complete cds | 0 |
| H11588 | Human mRNA for KIAA9001 | 1.154 |
| H11377 | Human mRNA for muscle phosphofructokinase (E.C. 2.7.1.11) | 1.325 |
| H16257 | Human endoglin mRNA, 3' end | 1.778 |
| H11719 | Human monocyte antigen CD14 (CD14) mRNA, complete cds | 0.969 |
| H11616 | Human brain glycogen phosphorylase mRNA, complete cds | 0.915 |

| H12238 | Human inosine-5'-monophosphate dehydrogenase (IMP) mRNA, complete cds | 2.017 |
|---|---|---|
| H11622 | human alpha-tubulin (from fetal brain) mrna | 1.04 |
| H11283 | Human cell adhesion protein (SQM1) mRNA, complete cds | 0 |
| H11110 | Homo sapiens macrophage migration inhibitory factor mRNA, 3' end | 0 |
| H12275 | Homo sapiens heart (R)-3-hydroxybutyrate dehydrogenase mRNA, 3' end | 0.583 |
| H11102 | H. sapiens ERF-1 mRNA 5' end | 0.614 |
| H11118 | Homo sapiens sui1iso1 mRNA, complete cds | 0.9 |
| H11984 | Human Na,K-ATPase alpha-subunit mRNA, complete cds | 0.453 |
| H14350 | H.sapiens mRNA for 17-beta-hydroxysteroid dehydrogenase | 0 |
| H15039 | Human acid sphingomyelinase (ASM) mRNA, complete cds | 0.943 |
| H15042 | Human melanoma antigen p15 mRNA, complete cds | 0 |
| H16173 | Human X-linked PEST-containing transporter (XPCT) mRNA, partial cds | 1.538 |
| H14381 | Human beta-polymerase mRNA, complete cds | 2.528 |
| H16078 | Human cadherin-associated protein-related (cap-r) mRNA, complete cds | 2.125 |
| H16183 | Human transcriptional repressor (CTCF) mRNA, complete cds | 0 |
| H15805 | Homo sapiens thyroid receptor interactor (TRIP3) mRNA, 3' end of cds | 1.131 |
| H16308 | Human transcription factor ETR101 mRNA, complete cds | 0.839 |
| H14811 | H.sapiens DROP9 mRNA | 1.223 |
| H16588 | Human extracellular signal-regulated kinase 1 mRNA, 3' end | 1.318 |
| H15438 | Human mRNA for Diff6, H5, CDC10 homologue | 1.324 |
| H16570 | Homo sapiens FK-506 binding protein homologue (FKBP38) mRNA, complete cds | 1.825 |
| H16704 | Human P311 HUM (3.1) mRNA, complete cds | 0 |
| H15336 | Human tyrosine kinase receptor (axl) mRNA, complete cds | 0 |
| H15340 | Human mRNA (KIAA0064) for ORF (novel protein), complete cds | 1.493 |
| H16710 | Homo sapiens G protein-coupled receptor kinase (GRK6) mRNA, complete cds | 1.418 |
| H15566 | H.sapiens alpha NAC mRNA | 2.099 |
| H15574 | Human erythropoietin receptor mRNA, complete cds | 1.96 |
| H15247 | H.sapiens (HepG2) LAL mRNA for lysosomal acid lipase | 1.66 |
| H29169 | H.sapiens mRNA for H+-ATP synthase subunit b | 0.74 |
| H28710 | Human gene for endothelin-B receptor (hET-BR) | 1.645 |
| H28711 | Human tetracycline transporter-like protein mRNA, complete cds | 0.746 |
| H15254 | Human prion protein mRNA, human PrP 27-30 mRNA, complete cds | 0 |

| | | |
|---|---|---|
| H29001 | H.sapiens mRNA for neuropeptide Y-like receptor | 0 |
| H29284 | H.sapiens mRNA for alpha 7B integrin | 1.283 |
| H28722 | Human ornithine decarboxylase antizyme (Oaz) mRNA, complete cds | 1.527 |
| H15137 | H.sapiens mRNA for carnitine acetyltransferase | 1.892 |
| H29455 | Human thymopoietin beta mRNA, complete cds | 2.082 |
| H28951 | Human ADP-ribosylation factor mRNA, complete cds | 1.149 |
| H15146 | H.sapiens nek3 mRNA for protein kinase | 0 |
| H15147 | Human polyposis locus (DP2.5 gene) mRNA, complete cds | 0 |
| H28988 | Human mRNA for cytochrome c oxidase subunit IV (EC 1.9.3.1) | 0.931 |
| H29482 | Human intercellular adhesion molecule 2 (ICAM-2) gene | 0 |
| H28708 | Human mRNA for liver pyruvate dehydrogenase (EC 1.2.4.1) E1' subunit | 0 |
| H17786 | Human phosphoglycerate kinase (pgk) gene | 0.805 |
| H17053 | Human interferon-gamma receptor mRNA, complete cds | 0 |
| H16957 | Human glyceraldehyde 3-phosphate dehydrogenase mRNA | 1.065 |
| H16737 | Human mRNA for purine nucleoside phosphorylase (PNP; EC 2.4.2.1) | 0.638 |
| H17855 | Human mRNA (KIAA0052) for ORF, partial cds | 1.106 |
| H17187 | Human mRNA for calretinin | 1.572 |
| H16775 | Homo sapiens protein tyrosine phosphatase (PRL-1) mRNA, 3' end of cds | 1.285 |
| H16990 | Homo sapiens nucleolysin TIAR mRNA, complete cds | 1.066 |
| H17467 | Human branched chain alpha-keto acid dehydrogenase mRNA, 3' end | 0 |
| H17193 | H.sapiens mRNA for 90K product | 0.98 |
| H16754 | Human natural killer cell enhancing factor (NKEFA) mRNA, complete cds | 0.79 |
| H17096 | H.sapiens PMI1 mRNA for phosphomannose isomerase | 1.286 |
| H17100 | Human nonerythroid alpha-spectrin (SPTAN1) mRNA, complete cds | 1.643 |
| H17425 | Human leukocyte adhesion protein (LFA-1/Mac-1/p150,95 family) beta subunit mRNA | 0 |
| H17383 | H.sapiens mRNA for ribosomal protein L3 | 1.59 |
| H16792 | Human mRNA for protein kinase C (PKC) type beta I | 0.822 |
| H16819 | Human mRNA for ZFM1 protein, complete cds | 1.031 |
| H17433 | Human nucleolin gene, complete cds | 1.081 |
| H17646 | H.sapiens EF-1delta gene encoding human elongation factor-1-delta | 1.543 |
| H16798 | Human mRNA (HA0643) for ORF (Canis oligosaccharyltransferase 48 kDa subunit homologue), complete cds | 1.157 |
| H17659 | Human 2',3'-cyclic-nucleotide 3'-phosphodiesterase gene | 0.59 |
| H19202 | H.sapiens mRNA for humer | 1.047 |

| H18816 | Homo sapiens cadherin-13 mRNA, complete cds | 1.117 |
|---|---|---|
| H18460 | Human aldehyde dehydrogenase 1 mRNA | 0.448 |
| H19016 | Human lipocortin II mRNA, complete cds | 2.666 |
| H19224 | Human type-1 protein phosphatase catalytic beta-subunit (PPP1CB) gene | 1.894 |
| H18473 | Human mRNA for MGC-24, complete cds | 1.05 |
| H19052 | Human voltage-dependent anion channel isoform 2 (VDAC) mRNA, complete cds | 0.686 |
| H19434 | Homo sapiens RHOA proto-oncogene multi-drug-resistance protein mRNA, 3' end | 1.217 |
| H18938 | Human aminoacylase-1 (ACY1) mRNA, complete cds | 1.11 |
| H20545 | Human hexokinase 1 (HK1) mRNA, complete cds | 0.866 |
| H20810 | Human mRNA for apoferritin H chain type | 0.475 |
| H22724 | Human oligodendrocyte-myelin glycoprotein (OMGP) mRNA, complete cds | 1.089 |
| H20530 | Human X box binding protein-1 (XBP-1) mRNA, complete cds | 0.611 |
| H20556 | Human mRNA for HHR23A protein, complete cds | 0.82 |
| H20845 | Human transducin beta-1 subunit mRNA, 3' end | 0.954 |
| H21068 | H.sapiens hH3.3B gene for histone H3.3 | 0.967 |
| H19424 | Human ribosomal protein L7a (surf 3) large subunit mRNA, complete cds | 1.974 |
| H20726 | Human casein kinase II beta subunit mRNA, complete cds | 1.528 |
| H20754 | H.sapiens mRNA for kinesin (heavy chain) | 2.103 |
| H21050 | H.sapiens TOP2 mRNA for DNA topoisomerase II (partial) | 1.451 |
| H19447 | H.sapiens HLTF-1 gene for helicase-like transcription factor | 1.85 |
| H20856 | Human DNA repair helicase (ERCC3) mRNA, complete cds | 1.19 |
| H22721 | Human mRNA for polyA binding protein | 1.983 |
| H22831 | Human unknown protein mRNA, partial cds | 1.434 |
| H22753 | Human (GH) germline c-myc proto-oncogene, 5' flank | 1.273 |
| H23074 | Human mRNA for mitochondrial 3-ketoacyl-CoA thiolase beta-subunit of trifunctional protein, complete cds | 1.15 |
| H23509 | Human mRNA for proteasome subunit HC2 | 0.914 |
| H22919 | Homo sapiens cystatin B mRNA, complete cds | 3.459 |
| H24236 | Human beta-2 microglobulin gene mRNA, 3' end | 2.611 |
| H23064 | Human ubiquinol cytochrome-c reductase core I protein mRNA, complete cds | 0 |
| H24446 | Human mRNA for ORF | 1.2 |
| H23457 | Human DNA for insulin-like growth factor II (IGF-2); exon 7 and additional ORF | 1.377 |
| H23490 | Human lamin B2 (LAMB2) mRNA, partial cds | 2.06 |
| H23277 | Human activin type II receptor mRNA, complete cds | 2.244 |
| H24391 | Human gene for C1-inhibitor | 2.599 |
| H24274 | Human mRNA for FGF-9, complete cds | 2.66 |

| H23180 | Homo sapiens cellular co-factor (RAB) gene, complete cds | 1.429 |
| --- | --- | --- |
| H29017 | H.sapiens mRNA for IFN-inducible gamma2 protein | 1.162 |
| H29322 | Homo sapiens cam kinase I mRNA, complete cds | 1.124 |
| H29776 | Human erythroblastosis virus oncogene homolog 2 (ets-2) mRNA, complete cds | 2.396 |
| H29609 | Human factor H homologue mRNA, complete cds | 2.722 |
| H29571 | Homo sapiens I-Rel mRNA, complete cds | 1.994 |
| H29778 | H.sapiens PC1 (NEC1) mRNA, complete cds | 0 |
| H29551 | Human mRNA for LCA-homolog. LAR protein (leukocyte antigen related) | 1.163 |
| H29583 | Human 35kD peroxisomal membrane protein mRNA, complete cds | 0 |
| H29313 | Human transcription factor IIIA (HTFIIIA) mRNA, partial cds | 1.658 |
| R15881 | Human m3 muscarinic acetylcholine receptor (CHRM3) gene, complete cds | 0 |
| R16045 | Human DNA-binding protein (CROC-1A) mRNA, complete cds | 1.987 |
| R16051 | Human leucine-rich protein mRNA, complete cds | 1.878 |
| R15449 | Homo sapiens amyloid protein homologue mRNA, complete cds | 1.544 |
| R15828 | Human calmodulin mRNA, complete cds | 1.288 |
| R15899 | Human casein kinase I delta mRNA, complete cds | 2.326 |
| R15759 | Human zinc finger protein (ZNF151) mRNA, partial cds | 2.385 |
| R15411 | Human lamin C mRNA, complete cds | 1.738 |
| R15998 | Human adenylyl cyclase mRNA, 3' end of cds | 2.29 |
| T66733 | Human transcobalamin II (TCII) mRNA, complete cds | 0 |
| T66735 | H.sapiens mRNA for NuMA protein | 1.644 |
| R15920 | Homo sapiens (clone S31i125) mRNA, 3' end of cds | 2.411 |
| R15905 | Human p18 protein mRNA, complete cds | 1.299 |
| T66753 | H.sapiens mRNA for laminin-binding protein | 1.773 |
| R15814 | Human malate dehydrogenase (MDHA) mRNA, complete cds | 1.173 |
| R15854 | Human TFIIIC Box B-binding subunit mRNA, complete cds | 1.429 |
| R16038 | Human transcription factor (TFIIB) mRNA, complete cds | 0.953 |

Signed and Sealed this

Tenth Day of September, 2002

*Attest:*

*Attesting Officer*

JAMES E. ROGAN
*Director of the United States Patent and Trademark Office*